US005750817A

United States Patent [19]

Tanaka et al.

[11] Patent Number: 5,750,817
[45] Date of Patent: *May 12, 1998

[54] PROCESS FOR PRODUCING α-OLEFIN OLIGOMERS AND α-OLEFIN OLIGOMER COMPOSITIONS

[75] Inventors: Eiji Tanaka, Kurashiki; Hisao Urata, Sagamihara; Toshiyuki Oshiki; Takayuki Aoshima, both of Yokohama; Riichirou Kawashima, Kurashiki; Shinji Iwade, Kurashiki; Hirofumi Nakamura, Kurashiki; Syunji Katsuki, Kurashiki; Takeshi Okano, Kurashiki, all of Japan

[73] Assignee: Mitsubishi Chemical Corporation, Japan

[*] Notice: The term of this patent shall not extend beyond the expiration date of Pat. Nos. 5,491,272 and 5,557,026.

[21] Appl. No.: 614,905

[22] Filed: Mar. 13, 1996

Related U.S. Application Data

[63] Continuation of Ser. No. 194,447, Feb. 9, 1994, abandoned.

[30] Foreign Application Priority Data

| Feb. 17, 1993 | [JP] | Japan | 5-028007 |
| Apr. 28, 1993 | [JP] | Japan | 5-103084 |
| Oct. 20, 1993 | [JP] | Japan | 5-286068 |

[51] Int. Cl.$^6$ ..................... C07C 2/02
[52] U.S. Cl. ............ 585/520; 585/511; 585/512; 585/521; 585/522; 585/523
[58] Field of Search .................. 585/511, 512, 585/520, 532, 500, 502, 521, 522, 523

[56] References Cited

U.S. PATENT DOCUMENTS

| 3,347,840 | 10/1967 | Manyik | 585/513 |
| 4,668,838 | 5/1987 | Briggs | 585/513 |
| 4,688,838 | 5/1987 | Briggs | 585/573 |
| 4,853,356 | 8/1989 | Briggs | 502/117 |
| 5,198,563 | 3/1993 | Reagen et al. | 556/57 |
| 5,376,612 | 12/1994 | Reagen et al. | 502/104 |
| 5,491,272 | 2/1996 | Tanaka et al. | 585/520 |
| 5,557,026 | 9/1996 | Tanaka et al. | 585/522 |

FOREIGN PATENT DOCUMENTS

| 0 237 079 | 9/1987 | European Pat. Off. . |
| 0 417 477 | 3/1991 | European Pat. Off. . |
| 0416304A2 | 3/1991 | European Pat. Off. . |
| 0 537 609 | 4/1993 | European Pat. Off. . |
| 0 780 353 A1 | 6/1997 | European Pat. Off. . |
| 93/0350 | 1/1993 | South Africa . |

OTHER PUBLICATIONS

Seidel et al "Uber die Darstellung neuer Phenylchrom–Komplexe" J. Anorg. All. Chem. vol. 404 1975 pp. 225–229.

Davies et al "Chromium (III) Chelates of Some 2–acylpyrroles" J. Inorg. Nucl. Chem., 1972, vol. 34 pp. 2791–2795.

Reagen "Chromium (II) and (III) Pyrrolyl Ethylene Oligomerization Catalysts . . . " Symposiums on Novel Preparation . . . American Chemical Society Miami Beach, Sep. 10–15, 1989, pp. 583–588.

Edema et al "The Unpredictable Structural Features . . . " Inorg. Chem. 1990, vol. 29, pp. 2147–2153.

Primary Examiner—Ponnathapura Achutamurthy
Attorney, Agent, or Firm—Nixon & Vanderhye

[57] ABSTRACT

The disclosure describes a process for preparing α-olefin oligomers, which comprises carrying out oligomerization of an α-olefin in a solvent by reacting said α-olefin in a chromium-based catalyst system composed of a combination of at least a chromium compound, an amine or metal amide, and an alkylaluminum compound, in a contacting mode that the chromium compound and the alkylaluminum compound are not previously contacted with each other.

42 Claims, No Drawings

PROCESS FOR PRODUCING α-OLEFIN OLIGOMERS AND α-OLEFIN OLIGOMER COMPOSITIONS

This is a continuation of application Ser. No. 08/194,447, filed 9 Feb. 1994, now abandoned.

BACKGROUND OF THE INVENTION

The present invention relates to a process for preparing α-olefin oligomers and α-olefin oligomer compositions. More particularly, it relates to an industrially advantageous process of preparation of α-olefin oligomers in which it is possible to produce α-olefin oligomers principally composed of 1-hexene from ethylene with high selectivity and in a high yield, and α-olefin oligomer compositions.

As an oligomerization process of α-olefins such as ethylene, etc., methods are known in which a chromium-based catalyst composed of a specific chromium compound and a specific organoaluminum compound is used as a catalyst. For instance, Japanese Patent Publication (KOKOKU) No. 43-18707 discloses a process for producing 1-hexene from ethylene by using a catalyst consisting of a chromium-containing VIA Group transition metal compound and a polyhydrocarbylaluminum oxide.

Also, in Japanese Patent Application Laid-Open (KOKAI) No. 3-128904 is disclosed a method for oligomerizing α-olefins by using a catalyst obtained by reacting a chromium-containing compound having chromium-pyrrolyl bond with an alkyl metal or a Lewis acid.

However, according to the process of Japanese KOKOKU No. 43-18707, the amount of the by-product polyethylene which is produced with 1-hexene is large, and if the trimerization reaction is carried out under the conditions which decrease yield of the by-product polyethylene, the catalyst activity is lowered.

Also, the method of Japanese KOKAI No. 3-128904 has the problem that the activity of the catalyst is unsatisfactory, although the yield of the by-products such as polyethylene, etc. is lowered. Further, in this method, there are required, in addition to the α-olefin oligomerization process, a step for preparing a chromium-containing compound at least having chromium-pyrrolyl bond from a chromium salt and metal pyrrolide, and a step for isolating the said chromium-containing compound, so that not only the oligomerization operations become too complicated but also the construction cost for the whole process is elevated. Moreover, it is very difficult to handle the chromium-containing compounds at least having chromium-pyrrolyl bond, since they are very unstable to air and to humidity.

As a result of the present inventors' earnest studies in order to solve the above-mentioned problems, it has been found that by carrying out oligomerization of an α-olefin in a solvent by reacting the α-olefin in a chromium-based catalyst system comprising a combination of at least a chromium compound, an alkylaluminum compound and an amine or a metal amide, in a contacting mode such that the chromium compound is not previously contacted with the alkylaluminum compound, α-olefin oligomers are obtained in a high yield. On the basis of this finding, the present invention has been attained.

SUMMARY OF THE INVENTION

An object of the present invention is to provide a process for producing α-olefin oligomers in which it is possible to prepare α-olefin oligomers such as 1-hexene in high selectivity and in a high yield without requiring any complicated operations.

Another object of the present invention is to provide an industrially advantageous process for producing 1-hexene.

Still another object of the present invention is to provide novel α-olefin oligomer compositions.

To achieve the aims, in a first aspect of the present invention, there is provided a process for producing α-olefin oligomers, comprising carrying out oligomerization of an α-olefin in a solvent by reacting the α-olefin in a chromium-based catalyst system comprising a combination of at least (a) a chromium compound, (b) an amine or metal amide, and (c) an alkylaluminum compound, in a contacting mode that the chromium compound and the alkylaluminum compound are not previously contacted with each other.

In a second aspect of the present invention, there is provided a process for producing α-olefin oligomers, comprising carrying out oligomerization of an α-olefin in a solvent by reacting the α-olefin in a chromium-based catalyst system comprising a combination of at least (a) a chromium compound, (b) an amine or metal amide, (c) an alkylaluminum compound, and (d) a non-coordinating Lewis acid-containing compound represented by the following formula (6) or (7)

wherein $M^1$ and $M^2$ are each an element selected from the group consisting of IIIB, IVB, VB and VIB groups in the periodic table; $R^1$ to $R^7$ are each an organic group, an inorganic group or an anionic atom; and $[L]^+$ denotes a cation including an element selected from the group consisting of IA, VIIA, VIII, IB and IIIB-VIB Groups in the periodic table.

In a third aspect of the present invention, there is provided an α-olefin oligomer composition obtained from oligomerization reaction of an α-olefin, and comprising not less than 85% by weight of 1-hexene and not more than 15% by weight of oligomers having not less the 10 carbon atoms and/or polymers.

In a fourth aspect of the present invention, there is provided a process for producing α-olefin oligomers, comprising carrying out oligomerization of an α-olefin in a solvent by reacting the α-olefin in a chromium-based catalyst system comprising a combination of at least (a) a chromium compound, (b) an amine or metal amide, (c) an alkylaluminum compound, and (e) a non-conjugated diene compound or (f) an aromatic hydrocarbon compound which may have an aliphatic hydrocarbon substituents, in a contacting mode that the chromium compound and the alkylaluminum compound are not previously contacted with each other.

DETAILED DESCRIPTION OF THE INVENTION

In the present invention, a catalyst comprising a combination of at least (a) a chromium compound, (b) an amine or metal amide, and (c) an alkylaluminum compound is used as chromium-based catalyst.

The chromium compound used in the present invention is represented by the formula: $CrX_n$, wherein X is an organic group, an inorganic group or an anionic atom; n is an integer of 1 to 6, and when n is not less than 2, X may be the same or different from each other. The valency of chromium is 0 to 6. Also, n in the above formula is preferably not less than 2.

The organic groups represented by X in the above formula include various kinds of groups having usually 1 to 30 carbon atoms. Typical examples of such organic groups having 1 to 30 carbon atoms are hydrocarbon groups, carbonyl group, alkoxy group, carboxyl group, β-diketonate group, β-ketocarboxyl group, β-ketoester group and amide groups. As the hydrocarbon groups having 1 to 30 carbon atoms, alkyl, cycloalkyl, aryl, alkylaryl, aralkyl and cyclopentadienyl may be exemplified. The inorganic groups include chromium salt-forming groups such as nitrate group and sulfate group. The anionic (negative) atoms include oxygen and halogens.

The preferred chromium compounds used in the present invention are chromium alkoxides, chromium carboxylates, chromium β-diketonates, salts of chromium with anions of β-ketoesters, and chromium halides. Specifically, chromium (IV) tert-butoxide, chromium (III) acetylacetonate, chromium (III) trifluoroacetylacetonate, chromium (III) hexafluoroacetylacetonate, chromium (III) (2,2,6,6-tetramethyl-3,5-heptanedionate), Cr(PhCOCHCOPh)$_3$ (wherein Ph represents phenyl group), chromium (II) acetate, chromium (III) acetate, chromium (III) 2-ethylhexanoate, chromium (III) benzoate, chromium (III) naphthenate, Cr (CH$_3$COCHCOOCH$_3$)$_3$, chromous chloride, chromic chloride, chromous bromide, chromic bromide, chromous iodide, chromic iodide, chromous fluoride and chromic fluoride may be exemplified.

Complexes composed of the above-mentioned chromium compounds and an electron donor can also be favorably used in the present invention. As the electron donor, a nitrogen-containing compound, an oxygen-containing compound, a phosphorus-containing compound and a sulfur-containing compound may be cited.

The nitrogen-containing compounds include nitriles, amines and amides. As typical examples thereof, acetonitrile, pyridine, dimethylpyridine, dimethylformamide, N-methylformamide, aniline, nitrobenzene, tetramethylethylenediamine, diethylamine, isopropylamine, hexamethyldisilazane and pyrrolidone may be exemplified.

The oxygen-containing compounds include esters, ethers, ketones, alcohols and aldehydes. As typical examples thereof, ethyl acetate, methyl acetate, tetrahydrofuran, dioxane, diethyl ether, dimethoxyethane, diethylene glycol dimethyl ether, triethylene glycol dimethyl ether, acetone, methyl ethyl ketone, methanol, ethanol and acetaldehyde may be exemplified.

As the phosphorus-containing compounds, hexamethylphosphoramide, hexamethyl phosphorus triamide, triethyl phosphite, tributylphosphine oxide and triethylphosphine may be exemplified.

As the sulfur-containing compounds, carbon disulfide, dimethyl sulfoxide, tetramethylene sulfone, thiophene and dimethyl sulfide may be exemplified.

Thus, as the complexes composed of chromium compounds and an electron donor, ether complexes, ester complexes, ketone complexes, aldehyde complexes, alcohol complexes, amine complexes, nitrile complexes, phosphine complexes and thioether complexes of chromium halides can be cited. More specifically, CrCl$_3$.3THF, CrCl$_3$.3dioxane, CrCl$_3$.(CH$_3$CO$_2$n-C$_4$H$_9$), CrCl$_3$.(CH$_3$CO$_2$C$_2$H$_5$), CrCl$_3$3(i-C$_3$H$_7$OH), CrCl$_3$.3[CH$_3$(CH$_2$)$_3$CH(C$_2$H$_5$)CH$_2$OH], CrCl$_3$.3pyridine, CrCl$_3$.2(i-C$_3$H$_7$NH$_2$), [CrCl$_3$.3CH$_3$CN].CH$_3$CN, CrCl$_3$.3PPh$_3$, CrCl$_2$.2THF, CrCl$_2$.2pyridine, CrCl$_2$2[(C$_2$H$_5$)$_2$NH], CrCl$_2$.2CH$_3$CN and CrCl$_2$.2[P(CH$_3$)2Ph] may be exemplified.

The chromium compound used in the present invention is preferably one which is soluble in hydrocarbon solvents. Examples of such chromium compounds are chromium β-diketonates, chromium carboxylates, salts of chromium with anions of β-ketoesters, chromium β-ketocarboxylates, chromium amide complexes, chromium carbonyl complexes, chromium carben complexes, various kinds of cyclopentadienyl complexes of chromium, chromium alkyl complexes and chromium phenyl complexes. As specific examples thereof, Cr(CO)$_6$, (C$_6$H$_6$)Cr(CO)$_3$, (CO)$_5$Cr(=CCH$_3$(OCH$_3$)), (CO)$_5$Cr(=CC$_6$H$_5$(OCH$_3$)), CpCrCl$_2$ (wherein Cp represents a cyclopentadienyl group), (Cp*CrClCH$_3$)$_2$ (wherein Cp* represents a pentamethylcyclopentadienyl group) and (CH$_3$)$_2$CrCl may be exemplified.

The chromium compound can be used in the form supported on a carrier such as an inorganic oxide, but it is preferably used in combination with other catalyst components without being supported on a carrier. In the present invention, the chromium-based catalyst is used in a specific contacting mode described later, and according to such contacting mode of process, it is possible to obtain a high catalyst activity, even if the chromium compound is not supported on a carrier. When the chromium compound is used without supporting it on a carrier, it is possible to dispense with the complicated operations required for supporting the chromium compound on a carrier and to avoid the problem of increase of the whole amount of catalyst used (the total amount of carrier and catalyst components combined) due to use of a carrier.

The amine used in the present invention is a primary or secondary amine. As the primary amines usable in the present invention, ammonia, ethylamine, isopropylamine, cyclohexylamine, benzylamine, aniline and naphthylamine may be exemplified. As the secondary amines usable in the present invention, diethylamine, diisopropylamine, dicyclohexylamine, dibenzylamine, bis(trimethylsilyl) amine, morpholine, imidazole, indoline, indol, pyrrole, 2,5-dimethylpyrrole, 3,4-dimethylpyrrole, 3,4-dichloropyrrole, 2,3,4,5-tetrachloropyrrole, 2-acylpyrrole, pyrazole and pyrrolidine may be exemplified.

The metal amide used in the present invention is one derived from a primary or secondary amine. Specifically, an amide obtained from the reaction of a primary or secondary amine and a metal selected from the group consisting of IA, IIA, IIIB and IVB Groups in the periodic table is usable. As such metal amides, lithium amide, sodium ethylamide, calcium diethylamide, lithium diisopropylamide, potassium benzylamide, sodium bis(trimethylsilyl)amide, lithium indolide, sodium pyrrolide, potassium pyrrolide, potassium pyrrolidide, diethylaluminum pyrrolide, ethylaluminum dipyrrolide and aluminum tripyrrolide may be exemplified.

In the present invention, a secondary amine, a metal amide derived from a secondary amine or a mixture thereof is preferably used. As preferred examples of the secondary amines used in the present invention, pyrrole, 2,5-dimethylpyrrole, 3,4-dimethylpyrrole, 3,4-dichloropyrrole, 2,3,4,5-tetrachloropyrrole and 2-acylpyrrole may be exemplified. As preferred examples of the metal amides derived from the secondary amines, diethylaluminum pyrrolide, ethylaluminum dipyrrolide, aluminum tripyrrolide, sodium pyrrolide, lithium pyrrolide and potassium pyrrolide may be exemplified. Of the pyrrole derivatives, those having a hydrocarbon group in the pyrrole ring are especially preferred.

The alkylaluminum compounds used in the present invention are those represented by the following formula (1):

$$R^1_m Al(OR^2)_n H_p X_q \quad (1)$$

wherein $R^1$ and $R^2$ are each a hydrocarbon group having usually 1 to 15 carbon atoms, preferably 1 to 8 carbon atoms, and they may be the same or different from each other; X is a halogen atom; m, n, p and q are the numbers defined by $0<m\leq3$, $0\leq n<3$, $0\leq p<3$ and $0\leq q<3$, respectively, and $m+n+p+q=3$.

The above-defined alkylaluminum compounds include the trialkylaluminum compounds represented by the following formula (2), the halogenated alkylaluminum compounds represented by the following formula (3), the alkoxyaluminum compounds represented by the following formula (4) and the alkylaluminum hydride compounds represented by the following formula (5)

$$R^1_3 Al \quad (2)$$

$$R^1_m AlX_{3-m} (1.5 \leq m < 3) \quad (3)$$

$$R^1_m Al(OR^2)_{3-m} \quad (4)$$

($0<m<3$, preferably $1.5 \leq m < 3$)

$$R^1_m AlH_{3-m} \quad (5)$$

($0<m<3$, preferably $1.5 \leq m < 3$)

As specific examples of the said alkylaluminum compounds, trimethylaluminum, triethylaluminum, triisobutylaluminum, diethylaluminum monochloride, diethylaluminum ethoxide and diethylaluminum hydride may be exemplified. Of these compounds, trialkylaluminum is especially preferred because of minimized formation of by-product polymers.

In the present invention, oligomerization of an α-olefin is carried out in a solvent by using a catalyst composed of the said catalytic components. It is indispensable to conduct oligomerization of an α-olefin by reacting the said α-olefin in a chromium-based catalyst system in a contacting mode that the chromium compound and the alkylaluminum compound are not previously contacted with each other. Due to such a specific contacting mode, trimerization reaction is allowed to take place selectively, enabling high-yield production of 1-hexene from ethylene as the starting material.

The said specific contacting mode can be materialized by various methods such as mentioned below (proviso that the term of "amine or metal amide" is represented by "amine"):

(1) an α-olefin and a chromium compound are introduced into a solution containing an amine and an alkylaluminum compound (contacting method A);

(2) an α-olefin and an alkylaluminum compound are introduced into a solution containing a chromium compound and an amine (contacting method B);

(3) an α-olefin, an amine and an alkylaluminum compound are introduced into a solution containing a chromium compound (contacting method C);

(4) an α-olefin, a chromium compound and an amine are introduced into a solution containing an alkylaluminum compound (contacting method D);

(5) a chromium compound, an amine, an alkylaluminum compound and an α-olefin are introduced into a reactor simultaneously and separately (contacting method E).

In the present invention, the expression of "in a contacting mode that the chromium compound and the alkylaluminum compound do not previously contact each other" means that not only the contact of the said two components is not allowed until the oligomerization reaction takes place but also when introducing the α-olefin and each components of the chromium-based catalyst into the reactor, additionally, this contacting mode is performed.

Each solution used in the above-described contacting methods is prepared by using a reaction solvent. In the present invention, the amount of a chromium compound is usually $1.0 \times 10^{-7}$ to 0.5 mol, preferably $1.0 \times 10^{-6}$ to 0.2 mol, more preferably $1.0 \times 10^{-5}$ to 0.05 mol based on one liter of solvent. On the other hand, the amount of an alkylaluminum compound is usually not less than 50 mmol, preferably, not less than 0.1 mol based on one mol of chromium compound in view of catalyst activity and trimer selectivity. The upper limit of the alkylaluminum compound is preferably $1.0 \times 10^4$ mol based on one mol of chromium compound. An amine or metal amide is used in an amount of usually not less than 0.001 mol, preferably 0.005 to 1,000 mol, more preferably 0.01 to 100 mol based on one mol of chromium compound.

In the present invention, the molar ratio of (a) the chromium compound, (b) the amine or metal amide, and (c) the alkylaluminum compound is preferably adjusted so that (a):(b):(c)=1:2 to 4:4 to 8, more preferably 1:2.5 to 3.5:4.5 to 6.5. By combining such specific conditions of molar ratio and reaction temperature (not more than 70° C.), it is possible to produce α-olefin oligomers, for example hexenes, in a yield of not less than 85% by weight, preferably 90% by weight (ratio to the total amount of products), and further, the selectivity of 1-hexene in the produced hexenes can be enhanced to 99% or more.

The reason why the activity of the oligomerization reaction of an α-olefin is lowered when a chromium-based catalyst is used in a contacting mode that the chromium compound and the alkylaluminum compound are allowed to contact with each other before taking place the oligomerization, is not yet clarified, but this may be accounted for as follows.

That is, it is considered that when the chromium compound and the alkylaluminum compound are contacted with each other, there takes place a ligand exchange reaction between the ligand coordinating to the chromium compound and the alkyl group in the alkylaluminum compound. The alkyl-chromium compound produced from such reaction is per se unstable which is unlike the alkyl-chromium compounds obtained in the ordinary ways. Therefore, the reduction and decomposition reaction of the alkyl-chromium compound is allowed to proceed preferentially, and consequently, demetallization improper to the α-olefin oligomerization reaction is induced, resulting in lowering of the α-olefin oligomerization reaction activity.

In the present invention, by jointly using as additive components: (d) a non-coordinating Lewis acid-containing compound, (e) a non-conjugated diene compound, or (f) an aromatic hydrocarbon compound which may have an aliphatic hydrocarbon substituent, it is possible to enhance selectivity (purity) of the produced α-olefin and catalyst activity, and to produce an α-olefin oligomers such as 1-hexene with high selectivity, without restricting the molar ratio of the chromium compound, the amine or metal amide, and the alkylaluminum compound as specified above. The reason for this is not yet clarified, but may be as follows.

As a non-conjugated diene coordinates to the chromium-based catalyst composed of a chromium compound, an amine or metal amide, and an alkylaluminum compound, generation of position isomers due to double bonds contained in the hexene is suppressed, so that purity of 1-hexene is elevated. It is considered that the same result is obtained with the aromatic hydrocarbon compound which may have an aliphatic hydrocarbon substituent. Also, coordination of a non-conjugated diene to the chromium atom increases the electron density on the chromium atom, resulting in an enhancement of oligomerization reaction activity of the electron-enriched chromium catalyst itself. In the case of the aromatic hydrocarbon compound having not less than three substituents of aliphatic hydrocarbon, the coordinating ability for the chromium catalyst elevates since the electron density on the aromatic ring is raised, and consequently, the oligomerization reaction activity of the electron-enriched chromium catalyst itself is enhanced.

On the other hand, in the case of a non-coordinating Lewis acid-containing compound, it is supposed that the non-coordinating Lewis acid-containing compound contributes to activation of the active species of the chromium-based catalyst or its precursor. In case of using a non-coordinating Lewis acid-containing compound, it is possible to produce α-olefin oligomers mainly composed of 1-hexene from ethylene with high selectivity and in a high yield even when the said contacting mode in the catalyst system comprising a combination of a chromium compound, an amine or metal amide, and an alkylaluminum compound is not performed. That is, the catalyst system comprising a combination of at least a chromium compound, an amine or metal amide, an alkylaluminum compound and a non-coordinating Lewis acid-containing compound is not restricted in its performance by the above-mentioned contacting mode of the α-olefin with the catalyst components and is capable of producing a high catalytic activity in the α-olefin trimerization reaction. Of course, in case of using a non-coordinating Lewis acid-containing compound, it is possible to perform the said contacting mode in the catalyst system comprising a combination of a chromium compound, an amine or metal amide, and an alkylaluminum compound. Also, the said compounds used as additional components may be added to the reaction system in whatever manner.

As the non-conjugated diene compound, there can be used chain non-conjugated dienes such as 1,5-hexadiene, 2,5-hexadiene, 1,6-diphenyl-2,5-hexadiene, 1,6-heptadiene, 2,5-heptadiene, 1,5-octadiene, 2,6-octadiene, 1,7-octadiene, etc., and cyclic non-conjugated dienes such as 1,5-cyclooctadiene, norbornadiene, dicyclopentadiene, 4-vinylcyclohexene, hexamethylbicyclo[2,2,0]hexadiene, 1,4-cyclohexadiene, 1,4-cycloheptadiene, etc. These dienes may have an aliphatic or aromatic hydrocarbon group such as alkyl, aralkyl or aryl group as a substituent. It is preferred to use a non-conjugated diene having not more than 20 carbon atoms. In view of the potent ability of coordination to the chromium atom, it is preferred to use a cyclic non-conjugated diene.

The amount of the non-conjugated diene compound used in the reaction of the present invention is not restricted in its upper limit provided that it is not less than 0.1 ppm, preferably not less than 10 ppm based on the amount of the charged solutions (the total amount of a solvent and non-conjugated diene compound). The said non-conjugated diene compound may be used as a solvent, but preferably it is used in an amount within the range of 0.1 to 20% by volume based on the amount of the charged solutions.

The aromatic hydrocarbon compounds having aliphatic hydrocarbon substituents are preferably divided into aromatic hydrocarbon compounds having not less than three substituents of aliphatic hydrocarbon and aromatic hydrocarbon compounds having not more than two substituents of aliphatic hydrocarbon. As the aliphatic hydrocarbon substituents, chain or alicyclic hydrocarbon groups such as methyl, ethyl, propyl, isopropyl, butyl, cyclopropyl, cyclobutyl and cyclohexyl may be exemplified.

As the aromatic hydrocarbon compounds having not less than three substituents of aliphatic hydrocarbon, 1,3,5-trimethylbenzene(mesitylene), 1,2,4-trimethylbenzene, 1,3,5-triethylbenzene, hexamethylbenzene, 1,3,5-triisopropylbenzene, 1,3,5-tri-t-butylbenzene, 1,2,4,5-tetramethylbenzene and 1,2,4,5-tetramethylnaphthalene may be exemplified.

The amount of the aromatic hydrocarbon compound having not less than three substituents of aliphatic hydrocarbon used in the reaction of the present invention is not restricted in its upper limit, provided that it is not less than 0.1 ppm, preferably not less than 10 ppm based on the amount of the charged solutions (the total amount of a solvent and an aromatic hydrocarbon compound). Such an aromatic hydrocarbon compound may be used as a solvent, but preferably it is used in an amount within the range of 0.1 to 95% by volume based on the amount of the charged solutions.

As the aromatic hydrocarbon compounds having not more than two substituents of aliphatic hydrocarbon, benzene, toluene, ethylbenzene, o-xylene, m-xylene, p-xylene, cumene, p-cymene, 1,4-dibutylbenzene, tert-butylbenzene, 1,4-di-tert-butylbenzene, cyclohexylbenzene, 1,4-dicyclohexylbenzene, methylnaphthalene, 2,6-dimethylnaphthalene and 1,5-dimethylnaphthalene may be exemplified.

The amount of the aromatic hydrocarbon compound having not more than two substituents of aliphatic hydrocarbon used in the reaction of the present invention is not restricted in its upper limit, provided that it is not less than 0.1 ppm, preferably not less than 10 ppm based on the amount of the charged solutions (the total amount of a solvent and an aromatic hydrocarbon compound). Such an aromatic hydrocarbon compound may be used as a solvent, but preferably it is used in an amount within the range of 0.1 to 95% by volume, preferably 0.5 to 40% by volume based on the amount of the charged solutions.

The non-coordinating Lewis acid-containing compounds used in the present invention are represented by the following formula (6) or (7):

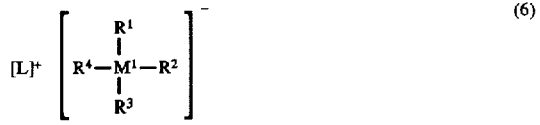

wherein $M^1$ and $M^2$ are each an element selected from the group consisting of IIIB, IVB, VB and VIB Groups in the periodic table, preferably B, Al or In; and $R^1$ to $R^7$ are each an organic group, an inorganic group or an anionic atom, which is hydrogen atom, dialkylamino group, alkoxy group having 1 to 20 carbon atoms, aryloxy group having 6 to 20 carbon atoms, alkyl group having 1 to 20 carbon atoms, aryl group having 6 to 20 carbon atoms, alkylaryl group having 7 to 20 carbon atoms, arylalkyl group having 7 to 20 carbon atoms, halogen-substituted hydrocarbon group having 1 to 20 carbon atoms, acyloxy group having 1 to 20 carbon atoms, alkoxyaryl group having 7 to 20 carbon atoms, halogen-substituted alkoxyaryl group having 7 to 20 carbon atoms, organic metalloid group, nitrate group or halogen atom. Two or more of these groups and/or atoms may be combined to form a ring.

As concrete examples of $R^1$ to $R^7$, dimethylamino group, diethylamino group, pyrrolyl group, 2,5-dimethylpyrrolyl group, methoxy group, ethoxy group, isopropoxy group, n-butoxy group, t-butoxy group, phenoxy group, 2,6-dimethylphenoxy group, 2,6-t-butylphenoxy group, naphthylphenoxy group, methyl group, ethyl group, n-propyl group, n-butyl group, n-octyl group, phenyl group, 3-methylphenyl group, 2,4-dimethylphenyl group, 2,6-dimethylphenyl group, 3,5-dimethylphenyl group, 2,3-dimethylphenyl group, 2,4,6-trimethylphenyl group, 2,3,5-trimethylphenyl group, 2,3,4-trimethylphenyl group, 3-t-butylphenyl group, 2,6-di-t-butylphenyl group, benzyl group, p-fluorophenyl group, 3,5-difluorophenyl group, pentachlorophenyl group, 3,4,5-trifluorophenyl group, pentafluorophenyl group, 3,5-di(trifluoromethyl)phenyl group, 3-methoxyphenyl group, 2,4-dimethoxyphenyl group, 2,6-dimethoxyphenyl group, 3,5-dimethoxyphenyl group, 2,3-dimethoxyphenyl group, 2,4,6-trimethoxyphenyl group, 2,3,5-trimethoxyphenyl group, 2,3,4-trimethoxyphenyl group, 3,5-bis(1-methoxy-2,2,2-trifluoro-1-(trifluoromethyl)ethyl) phenyl group, 3-(1-methoxy-2,2,2-trifluoro-1-(trifluoromethyl)ethyl-5-(trifluoromethyl)phenyl group, 3-(2,2,2-trifluoro-1-(2,2,2-trifluoroethoxy)-1-(trifluoromethyl)ethyl)-5-(trifluoromethyl)phenyl group, 3,5-bis(2,2,2-trifluoro-1-(2,2,2-trifluoroethoxy))-1-(trifluoromethyl)ethyl)phenyl group, trimethylsilyl group, trimethylgermyl group, diphenylarsine group, dicyclohexylantimony group, pentafluorotelluroxy group, F, Cl, Br and I can be exemplified.

[L]+ in the formula (6) denotes a cation containing an element selected from the group consisting of IA, VIIA, VIII, IB and IIIB to VIB Groups in the periodic table. L is represented by $M^3$, $M^4R^8R^9$, $E^1R^{10}R^{11}R^{12}$ or $E^2R^{13}R^{14}R^{15}R^{16}$, wherein $M^3$ is an element selected from the group consisting of IA, IB and IIIB Groups in the periodic table, $M^4$ is an element selected from the group consisting of VIIA and VIII Groups in the periodic table, $E^1$ is carbon atoms, oxygen atom or sulfur atom, and $E^2$ is nitrogen atom or phosphorus atom.

$M^3$ is preferably Li, Na, K or Ag, and $M^1$ is preferably Mn, Fe, Co or Ni.

$R^8$ and $R^9$ are each a substituent group selected from the group consisting of cyclopentadienyl group, substituted cyclopentadienyl group, indenyl group and fluorenyl group. $R^8$ and $R^9$ may be combined to form a ring. The substituent of the substituted cyclopentadienyl group of $R^8$ and $R^9$ is usually an alkyl group having 1 to 6 carbon atoms, and the number of the substituents is an integer of 1 to 5. As such substituted cyclopentadienyl groups, methylcyclopentadienyl, n-butylcyclopentadienyl and pentamethylcyclopentadienyl may be exemplified.

$R^{10}$ to $R^{16}$ are each a substituent group selected from the group consisting of hydrogen atom, halogen atom, alkyl group having 1 to 20 carbon atoms, aryl group having 6 to 20 carbon atoms, alkylaryl group having 7 to 20 carbon atoms, arylalkyl group having 7 to 20 carbon atoms or organic metalloid group. As concrete example of $R^{10}$ to $R^{16}$, hydrogen atom, methyl group, ethyl group, n-propyl group, n-butyl group, n-octyl group, cyclohexyl group, phenyl group, benzyl group, 3-methylphenyl group, 2,4-dimethylphenyl group, 2,6-dimethylphenyl group, 3,5-dimethylphenyl group, 2,3-dimethylphenyl group, 2,4,6-trimethylphenyl group, 2,3,5-trimethylphenyl group, 2,3,4-trimethylphenyl group, 3-t-butylphenyl group, 2,6-di-t-butylphenyl group, F, Cl, Br and I may be exemplified.

In the compounds represented by the formula (6) or (7) those in which $M^1$ or $M^2$ is boron are preferred.

Of the compounds represented by the formula (6), the following compounds are especially preferred.

As compounds wherein L is $M^3$, silver tetraphenylborate, sodium tetraphenylborate, silver tetrakis(pentafluorophenyl) borate, lithium tetrakis(pentafluorophenyl)borate, silver tetrakis(pentafluorotelluroxy)borate, silver tetrafluoroborate, silver tetrafluoroarsenate and silver tetrafluoroantimonate may be exemplified.

As compounds wherein L is $M^4R^8R^9$, ferrocenium tetraphenylborate, manganese tetraphenylborate (tetraphenylporphyrin), ferrocenium tetrakis (pentafluorophenyl)borate, decamethylferrocenium tetrakis (pentafluorophenyl)borate, acetylferrocenium tetrakis (pentafluorophenyl)borate, formylferrocenium tetrakis (pentafluorophenyl)borate and cyanoferrocenium tetrakis (pentafluorophenyl)borate may be exemplified.

As compounds wherein L is $E^1R^{10}R^{11}R^{12}$, trityl tetraphenylborate, trityl tetrakis(pentafluorophenyl)borate, trimethylsulfonium tetraphenylborate, benzyldimethylsulfonium tetraphenylborate and benzyldimethylsulfonium tetrakis(pentafluorophenyl)borate may be exemplified.

As compounds wherein L is $E^2R^{13}R^{14}R^{15}R^{16}$, ammonium tetraphenylborate, triethylammonium tetraphenylborate, tri (n-butyl)ammonium tetraphenylborate, trimethylammonium tetraphenylborate, pyrrolium tetraphenylborate, 2,5-dimethylpyrrolium tetraphenylborate, ammonium tetrakis (pentafluorophenyl)borate, triethylammonium tetrakis (pentafluorophenyl)borate, tri(n-butyl)ammonium tetrakis (pentafluorophenyl)borate, trimethylammonium tetrakis (pentafluorophenyl)borate, anilinium tetrakis (pentafluorophenyl)borate, monomethylanilinium tetrakis (pentafluorophenyl)borate, dimethylanilinium tetrakis (pentafluorophenyl)borate, tetraphenylphosphonium tetrakis (pentafluorophenyl)borate, tetrabutylammonium tetrakis (pentafluorophenyl)borate, methyldiphenylammonium tetrakis(pentafluorophenyl)borate, triphenylammonium tetrakis(pentafluorophenyl)borate, pyridinium tetrakis (pentafluorophenyl)borate, dimethyl(m-nitroanilinium) tetrakis(pentafluorophenyl)borate, dimethyl(p-bromoanilinium) tetrakis(pentafluorophenyl)borate, (p-cyanopyridinium) tetrakis(pentafluorophenyl)borate, trimethylanilinium tetrakis(pentafluorophenyl)borate, (N-methylpyridinium) tetrakis(pentafluorophenyl)borate, trimethylsulfinium tetrakis(pentafluorophenyl)borate, (o-cyano-N-methylpyridinium) tetrakis(pentafluorophenyl) borate, dimethyldiphenylammonium tetrakis (pentafluorophenyl)borate, (p-cyano-N-benzylpyridinium) tetrakis(pentafluorophenyl)borate, methyltriphenylammonium tetrakis(pentafluorophenyl)borate, pyrrolium tetrakis (pentafluorophenyl)borate, 2,5-dimethylpyrrolium tetrakis (pentafluorophenyl)borate, dimethylanilinium tetrakis(3,5-di(trifluoromethyl)phenyl)borate, triethylammonium hexafluoroarsenate, dimethylanilinium tetrakis(3,5-bis(1-methoxy-2,2,2-trifluoro-1-(trifluoromethyl)ethyl)) phenylborate, dimethylanilinium tetrakis(3-(1-methoxy-2,2, 2-trifluoro-1-(trifluoromethyl)ethyl)-5-(trifluoromethyl) phenylborate, dimethylanilinium tetrakis(3-(2,2,2-trifluoro-1-(2,2,2-trifluoroethoxy)-1-(trifluoromethyl)ethyl)-5-(trifluoromethyl))phenylborate, dimethylanilinium tetrakis (3,5-bis(2,2,2-trifluoro-1-(2,2,2-trifluoroethoxy)-1-(trifluoromethyl)ethyl)phenylborate, tetraethylammonium tetraphenylborate, methyltri(n-butyl)ammonium tetraphenylborate, benzyltri(n-butyl)ammonium tetraphenylborate, trimethylanilinium tetraphenylborate, dimethyldiphenylammonium tetraphenylborate, methyltriphenylammonium tetraphenylborate, methylpyridinium tetraphenylborate, benzylpyridinium tetraphenylborate, methyl(2-cyanopyridinium) tetraphenylborate, tetraethylammonium tetrakis(pentafluorophenyl)borate, methyltri(n- butyl)ammonium tetrakis(pentafluorophenyl)borate, benzyltri(n-butyl)ammonium tetrakis(pentafluorophenyl) borate, methyl(4-cyanopyridinium) tetrakis (pentafluorophenyl)borate and benzylpyridinium tetrakis (pentafluorophenyl)borate may be exemplified.

Of the compounds represented by the formula (7), tris (pentafluorophenyl)boron, tris(3,5-bis(1-methoxy-2,2,2-trifluoro-1-(trifluoromethyl)ethyl)phenyl)boron, tris-3-methoxy-2,2,2-trifluoro-1-(trifluoromethyl)ethyl)-5-(trifluoromethyl)phenylboron, tris(3-(2,2,2-trifluoro-1-(2,2,2-trifluoroethoxy)-1-(trifluoromethyl)ethyl)-5-(trifluoromethyl))phenylboron, tris(3,5-bis(2,2,2-trifluoro-1-(2,2,2-trifluoro-1-(2,2,2-trifluoroethoxy)-1-(trifluoromethyl)ethyl)phenylboron, triphenylboron, tris (pentafluorotelluroxy)boron and the like are especially preferred.

A non-coordinating Lewis acid-containing compound is usually used in an amount within the range of not less than 0.001 mol, preferably 0.005 to 1,000 mol, more preferably 0.01 to 100 mol based on one mol of the chromium compound.

As the α-olefin used as starting material in the present invention, substituted or non-substituted α-olefins having 2 to 30 carbon atoms are usable. As such α-olefins, ethylene, propylene, 1-butene, 1-hexene, 1-octene, 3-methyl-1-butene and 4-methyl-1-pentene may be exemplified. Ethylene is especially preferred since it is possible to produce 1-hexene as a trimer at a high selectivity and in a high yield.

As the solvent used in the reaction of the present invention, there can be used chain or alicyclic saturated hydrocarbons having 1 to 20 carbon atoms such as butane, pentane, 3-methylpentane, hexane, heptane, 2-methylhexane, octane, cyclohexane, methylcyclohexane, decalin, etc.; aromatic hydrocarbons such as benzene, toluene, xylene, ethylbenzene, mesitylene, tetralin, etc.; chain chlorinated hydrocarbons such as chloroform, carbon tetrachloride, methylene chloride, dichloroethane, trichloroethane, tetrachloroethane, etc.; chlorinated aromatic hydrocarbons such as chlorobenzene, dichlorobenzene, etc. These solvents may be used either singly or as a mixture. The α-olefin used as the starting material for the reaction or the α-olefins other than the main starting material for the reaction can also be used as solvent. An α-olefin having 4 to 30 carbon atoms, especially an α-olefin which is liquid at room temperature is preferred as a solvent. As general solvent, a chain saturated hydrocarbon having not more than 7 carbon atoms, preferably 4 to 7 carbon atoms is preferably used. Alicyclic saturated hydrocarbons are also preferred. Use of a solvent such as mentioned above proves helpful for suppressing formation of the by-product polymers. Further, in case of using an alicyclic hydrocarbon, a high catalytic activity can be obtained. As typical examples of the saturated hydrocarbons having not more than 7 carbon atoms, propane, butane, pentane, hexane or heptane may be exemplified. These solvents may have a branched chain structure.

Reaction temperature is usually 0° to 250° C., preferably 10° to 150° C., more preferably 25° to 70 ° C. Reaction pressure can be suitably selected from between ordinary pressure and 250 kg/cm$^2$, but usually a pressure between ordinary pressure and 100 kg/cm$^2$ is sufficient. Reaction time is usually one minute to 20 hours, preferably 0.5 to 6 hours. The type of reaction may be batchwise, semi-batchwise or continuous. Presence of hydrogen in the reaction system is preferable since the catalytic activity is enhanced as well as objective trimer selectivity. Pressure of the co-existent hydrogen is usually 0.1 to 100 kg/cm$^2$, preferably 1 to 80 kg/cm$^2$.

In the case of continuous reaction, the said specific contact can be performed in the different zones. In this case, a reactor or a one-stage or multi-stage mixing tank is used as reaction vessel. A tubular reactor is a reaction apparatus comprising a straight pipe, a coiled or U-shaped curved pipe designed such that the reactants are introduced from one end thereof and the reaction product is discharged from the other end. Multi-stage mixing tank is a reaction apparatus in which, basically, the reactants are introduced initially into the first of the plural sets of mixing tank arranged in series to each other, the introduced reactants being transferred into the ensuing tanks successively, and the reaction product is discharged out from the final tank.

In the present invention, in case of using a tubular reactor, a part of the reactants is introduced in a front portion (end) of the straight or curved pipe, and the rest of the reactants is introduced in a back point (portion) of the introducing portion of a part of the reactants and in the first half thereof. For instance, an amine or metal amide, and an alkylaluminum compound are introduced in the front end of the tubular reactor and an α-olefin and a chromium compound are introduced in a back portion of the introducing portion of the amine or metal amide, and the alkylaluminum compound. Alternatively, a chromium compound, and an amine or metal amide may be introduced from the front end of the tubular reactor, and an α-olefin and an alkylaluminum compound are introduced in a back portion of the introducing portion of the chromium compound, and the amine or metal amide. In use of a tubular reactor, the reactant introducing points may be provided in any desired number as far as an α-olefin and a chromium-based catalyst are contacted with each other in a contacting mode that the chromium compound and the alkylaluminum compound are not previously contacted with each other.

In case of using a multi-stage mixing tank assembly in the present invention, for example, an amine or metal amide, and an alkylaluminum compound are introduced into the first tank, and an α-olefin and a chromium compound are introduced into the second tank. Also, a chromium compound and an amine or metal amide may be introduced into the first tank, and an α-olefin and an alkylaluminum compound are introduced into the second tank. In this case, there may be provided any desired number of mixing tanks as far as an α-olefin and a chromium-based catalyst are contacted with each other in a contacting mode that the chromium compound and the alkylaluminum compound are not contacted with each other.

In the present invention, an antistatic agent inert to the catalyst components is allowed to exist in the reaction mixture, thereby preventing deposition of the by-product polymer to the reactor, distillation column, other incidental equipment, and piping. The "antistatic agent inert to the catalyst components" means an antistatic agent whose the presence thereof in the reaction system does not affect the activity of the said chromium-based catalyst. As such antistatic agent, those already proposed in the field of polymerization of α-olefins can be used in the present invention. For example, the antistatic agents disclosed in Japanese Patent Publication (KOKOKU) No. 50-38158, namely polyvalent metal salts of the organic acids having a molecular weight of at least 300, more specifically polyvalent metal alkylsalicylates, polyvalent metal sulfonated dialkyl aliphatic dicarboxylates and the like can be used. The alkyl group of alkylsalicylic acids is specifically one having 14 to 18 carbon atoms. The polyvalent metals usable here include magnesium, copper, zinc, cadminum, aluminum, lead, chromium, molybdenum, manganese and the like. The polyvalent metal salts may be used either singly or as a mixture thereof. They may also be used as an admixture with a high polymeric electrolyte.

As the high polymeric electrolytes usable in the present invention, stearyl methacrylate/methacrylic acid copolymer, β-hydroxyethyl methacrylate/stearyl methacrylate/ methacrylic acid copolymer, ethyleneimine polymers, 2-methyl-5-vinylpyridine polymers, copolymer of 2-methyl-5-vinylpyridine and mixture of lauryl methacrylate and stearyl methacrylate and lauryl methacrylate/stearyl methacrylate/ methyl methacrylate/2-methyl-5-vinylpyridine polymer may be exemplified. Copolymer of 2-methyl-5-vinylpyridine and lauryl methacrylate (carbon atoms of the alkyl group: 16–18) is especially preferred. "ASA-3" (produced by Shell Chemical Co.) as an antistatic agent can be favorably used in the present invention. This commercial product is an antistatic agent comprising about 20 wt % of chromium (III) alkylsalicylates having 14 to 18 carbon atoms, about 10 wt % of calcium salt of di-2-ethylhexyl sulfosuccinate, about 45 wt % of a copolymer of 2-methyl-5-vinylpyridine and $C_{17}$ alkyl ester of methacrylic acid (high polymeric electrolyte) and about 25 wt % of m-xylene.

As other example of antistatic agent usable in the present invention, there can be cited the antistatic agent disclosed in Japanese Patent Publication No. 56-51164, which is a composition containing (i) a polysulfone copolymer of sulfur dioxide and an olefin-based compound, (ii) a polymer-like polyamine which is the reaction product of epichlorohydrin and aliphatic primary monoamine or N-aliphatic hydrocarbylalkylenediamine and (iii) an oil-soluble sulfonic acid. As oil-soluble sulfonic acid, alkanesulfonic acid, petroleum sulfonic acid and the like can be used. This composition preferably contains a solvent selected from benzene, toluene, xylene, cyclohexane, fuel oil, isobutane and a mixture thereof. As for the contents of the said components (i) to (iii) and solvent in this composition, it is stated that (i) the polysulfone copolymer is 5–25 wt %, (ii) the polymer-like polyamine is 5 to 25 wt %, (iii) the oil-soluble sulfonic acid is 5 to 30 wt %, and the solvent is 20 to 85 wt %.

"Stadis 450" and "Stadis 425" (produced by E. I. Du Pont de Nemours & Co.) as antistatic agents can be favorably used as an antistatic agent in the present invention. "Stadis 450" is a composition comprising about 14 wt % of polybutene sulfate, about 3 wt % of aminoethanolepichlorohydrin polymer, about 13 wt % of alkylbenzenesulfonic acid, about 70 wt % of toluene and trace amounts of quaternary ammonium salt of aliphatic alkyl and propyl alcohol. "Stadis 425" is a composition comprising 2 to 7 wt % of polyaminopolyol, 2 to 8 wt % of dodecylbenzenesulfonic acid, 60 to 70 wt % of kerosine, 10 to 20 wt % of toluene, less than 0.017 wt % of benzene and 2 to 7 wt % of mixed aromatic solvent ($C_{9-17}$).

Further, the antistatic agents disclosed in Japanese Patent Publication (KOKOKU) No. 63-66321, that is, (I) higher fatty acid soaps represented by the formula: RCOOM (wherein R is a $C_{12-22}$ saturated or unsaturated hydrocarbon group; M is an alkali or alkaline earth metal); (II) sulfuric acid esters of higher alcohols represented by the formula: $ROSO_3M$ (wherein R and M are as defined above), sulfuric acid esters of secondary higher alcohols represented by the formula: $R(R)CHOSO_3M$ (wherein R and M are as defined above); (III) alkali or alkaline earth metal salts of the reaction product of castor oil, olive oil, peanut oil, cottonseed oil or the like and sulfuric acid; (IV) alkali or alkaline earth metal salts of compounds of polyhydric alcohols and higher fatty acids in which the residual OH groups have been turned into sulfuric acid esters with the partial esters of the said polyhydric alcohols and higher fatty acids; (V) sulfuric acid ester salts of higher fatty acid alkylolamides represented by the formula: $RCONH(CH_2)_n$ (wherein R and M are as defined above; n is an integer of 1 to 10); (VI) compounds represented by the formula: $R(OCH_2CH_2)_nOSO_3$ (wherein R, M and n are as defined above); (VII) higher alkyl sulfonates represented by the formula: $RSO_3M$ (wherein R and M are as defined above); (VIII) alkylallyl sulfonates; (IX) condensates of compounds represented by the formula: RCOCl and compounds represented by the formula: $RNH(CH_2)_nSO_5M$ (wherein R, M and n are as defined above); (X) condensates of compounds of the formula: RCOCl and compounds represented by the formula: $HO(CH_2)_nSO_3M$ (wherein R, M and n are as defined above); (XI) alkali or alkaline earth metal salts of dialkylsulfosuccinic acid; and (XII) alkali or alkaline earth metal salts of partial esters of higher alcohols and phosphoric acid. Among these antistatic agents, alkaline metal salts of dialkylsulfosuccinic acid are preferred.

An antistatic agent is introduced into the reactor along with the starting material α-olefin, catalyst components and solvent, or it is mixed with these components and then introduced into the reactor. In case the reaction is carried out batchwise, antistatic agent may be added into the reaction mixture composed of the above-mentioned components in a relatively early phase of the reaction. The concentration of antistatic agent in the reaction mixture is usually 0.003 to 30 mg/l, preferably 0.01 to 2 mg/l based on one liter of the reaction mixture.

In the present invention, it is preferred that oligomerization of an α-olefin is carried out at a temperature of 0° to 70° C. by using a saturated hydrocarbon having not more than 7 carbon atoms as solvent. This process allows easy separation of the by-product polymers. That is, when the reaction is conducted under the above conditions, the by-product polymers take a granular form and can be easily separated.

The by-product polymers in the reaction mixture are separated out without allowing them to melt. The granular by-product polymers can be very easily separated out as compared with conventional polymer separation. Further, the granular by-product polymers are scarcely deposited on the inner wall of the piping, so that it is possible to avoid such problems as blocking of the piping and reduction of heat transfer coefficient. If the reaction mixture is stirred to disperse the by-product polymers prior to their separation, it is possible to control the grain size of the granular by-product polymers.

Stirring of the reaction mixture can be conducted by any suitable means, for example, a rotary blade stirrer, a blow stirrer using an inert gas or a circulation pump system, but usually a rotary blade stirrer is employed. The shape of the blade in the rotary blade stirrer may be suitably selected from various known types such as turbine type, fan turbine type, curved blade fan turbine type, propeller type, simple paddle type (flat blade type), gate type, shutter type, etc. If necessary, a baffle plate may also be used along with rotary blade stirrer, if necessary.

In case a rotary blade stirrer is used, the grain size of the granular by-product polymers differs according to the stirring speed (shearing force), that is, the grain size becomes small when the stirring speed is increased, while the grain size is enlarged when the stirring speed is lowered. Usually the preferred grain size of the granular by-product polymers is 100 to 3,000 μm, more preferably 300 to 1,000 μm. Therefore, the stirring speed (shearing force) of the rotary blade stirrer is preferably so selected that the grain size of the granular by-product polymers will fall within the above-defined range.

The specific stirring speed differs depending on the factors relating to stirring element, such as shape of the blade, blade length, blade width, slat angle, number of slats, slat mounting height, etc. the factors relating to oligomerization reactor, such as diameter of oligomerization reactor (autoclave), depth of reaction mixture, width of baffle plate, number of baffle plates used, etc., and the factors relating to reaction mixture, such as density, viscosity, etc., so that it is necessary to determine the appropriate stirring speed by a contacting model test before carrying out the oligomerization reaction. In the case of a one-stage simple paddle type (flat blade type) stirrer, the grain size of the granular by-product polymers can generally be controlled to fall within the range of 100 to 3,000 µm by adjusting the stirring speed to 200 to 1,000 r.p.m.

Separation of the by-product polymers can be accomplished by using a known solid/liquid separator. In the present invention, a filter or a centrifuge is preferably used. In the case of the granular by-product polymers, separation thereof can be accomplished with surprising easiness by using a solid/liquid separator of a structure in which the solid matter is separated by centrifugation while discharging the separated solid matter out of the system by a rotary screw.

A solid/liquid separator of the above-described specific structure is per se known. For example, this type of separator is commercially available under the trade name of "Sharples Super Decanter" (manufactured by Tomoe Kogyo Co., Ltd.). Also, various types of screw-adapted centrifuges are marketed by Ishikawajima Harima Industrial Co., Ltd.

The said solid/liquid separator is mainly composed of an external bowl having a shape of a cylinder and a cone combined integrally with each other, the said bowl being supported at its both ends by bearings and provided with a discharge port for separating liquid and solid matter, an internal screw disposed inside of the said bowl coaxially therewith, and having provided therearound a screw blade and a plurality of liquid spouts in the body portion, a feed pipe for feeding the stock solution through the liquid spouts in the body portion of the said internal screw, a rotatory mechanism (planetary gears) designed to produce a rotational difference between the said external bowl and internal screw in the same direction, and a casing enclosing said external bowl, and having a discharge port for separating liquid and solid matter. There are two types of separator such as a vertical separator and horizontal separator.

In operation of the above solid/liquid separator, the external bowl is rotated at high speed while the internal screw is rotated at a lower speed, whereby the stock solution supplied from the feed pipe is centrifuged, with the solid matter being separated to the wall surface side of the said bowl and discharged out of the system by the conveying action of the screw. In the present invention, the operating conditions of the said solid/liquid separator are not subjected to any specific restrictions, but usually the external bowl is operated at a speed of 2,000 to 6,000 r.p.m., while the internal screw is operated at a speed about 500 to 1,000 r.p.m. lower than the speed of the external bowl.

The α-olefin oligomers yielded after separation of the by-product polymers in the reaction mixture is purified, if necessary. Usually distillation is employed for purification, and this allows recovery of the objective substance with high purity.

In the present invention, part of the obtained α-olefin oligomers may be converted into a saturated hydrocarbon by hydrogenation and such saturated hydrocarbon may be recycled to the oligomerization reaction system to realize a significant reduction of solvent cost. The fraction of the α-olefin oligomers to be subjected to the hydrogenation treatment is not specifically defined, but it is preferred to separate the product into a fraction with carbon atoms of 4 to 6 and a fraction with carbon atoms of not less than 8 by distillation and to subject the fraction with carbon atoms of not less than 8 to the hydrogenation treatment.

The amount of the α-olefin oligomers to be subjected to hydrogenation may be such as equivalent to the amount lost in the steps of oligomerization reaction, separation of the by-product polymers and distillation. In case the α-olefin oligomers with carbon atoms of not less than 8 is subjected to the hydrogenation treatment according to the said preferred operation mode, since the yield of the α-olefin oligomers with carbon atoms of not less than 8 is relatively small in the oligomerization reaction of the present invention, it is possible to obtain a saturated hydrocarbon of an amount equivalent to the loss of the reaction solvent if the whole amount of said α-olefin oligomers is subjected to the hydrogenation treatment.

Thus, hydrogenation of the α-olefin oligomers is performed for converting the α-olefin contained in the said oligomers into a saturated hydrocarbon. For performing such hydrogenation, the generally known hydrogenation treatment conditions can be employed. For example, the α-olefin oligomers is subjected to hydrogenation treatment by using a platinum catalyst supported on γ-alumina at a temperature of 30° to 150° C. under a pressure of 10 to 70 kg/cm$^2$. However, the hydrogenation treatment conditions usable in the present invention are not limited to the above-described.

Other fractions of α-olefin oligomers, for example, one with carbon atoms of 4 to 6 is further purified by distillation and recovered as a high-purity objective product. In the present invention, especially high-purity 1-hexene can be produced from ethylene in an industrially advantageous way.

In the present invention, distillation for separating α-olefin oligomers may not necessarily be conducted on all of the substances in the reaction mixture. For instance, in case of producing 1-hexene from ethylene, small quantities of other α-olefin oligomers such as 1-octene may be left in the reaction mixture without separation. Also, the by-products such as $C_{10-20}$ compounds may be left in the reaction mixture.

In the present invention, the catalyst components such as chromium compound contained in the reaction mixture may be removed to enhance purity of the obtained α-olefin oligomers. The various substances obtained from the oligomerization reaction of α-olefins can be applied to various uses. For instance, 1-hexene, 1-butene and 1-octene which are recovered from distilled α-olefin oligomer composition can be used as a starting monomer for preparation of useful polymers such as linear low-density polyethylene (L-LDPE). Also, 1-butene or butane of $C_4$, 1-octene or octane of $C_8$, etc., can be converted into corresponding sulfonic acids derivatives by adding hydrogen sulfide and oxidizing the resultant mixture. Salts of such sulfonic acids are useful as surfactant.

Thus, trying to enhance purity of the produced α-olefin oligomers by removing the catalyst components such as chromium compound contained in the reaction mixture is important in use of the various substances obtained from the oligomerization reactions of α-olefins. Further, depending on the conditions of distillation separation of the substances, there may arise the problems such as deposition of the catalyst components such as chromium compound on distillation column, so that it is necessary, from such aspect, to remove the catalyst components such as chromium compound contained in the reaction mixture.

Removal of the catalyst components contained in the reaction mixture can be accomplished by contacting the reaction mixture containing the catalyst components with an aqueous acidic or alkaline solution. Removal of the catalyst components is preferably conducted after separation of the by-product in the reaction mixture. As acid, nitric acid, hydrochloric acid and sulfuric acid is preferably used. As alkali, sodium hydroxide is preferably used. Such acid or alkali is usually used in the form of a 2 to 20 wt % aqueous solution. Contact of the reaction mixture containing the catalyst components with an acid or alkali solution can be accomplished by using various types of extractor, but it is preferred to use an apparatus composed of a stirring tank and a stationary separating tank. Such tanks may be arranged in single stage or multiple stages. The extraction system may be either batchwise or continues.

The catalyst components easily removed by the said extraction, although variable depending on the type of extracting agent used (acid or alkali aqueous solution), are mostly metallic substances such as chromium compound, metal amide and alkylaluminum compound. In the present invention, if necessary, there may be used two stirring tanks to perform extraction with both an acidic aqueous solution and an alkaline aqueous solution.

The extracting conditions are not critical, but in case of using stirring tank and stationary separating tank, the oil layer to aqueous layer ratio in the stirring tank is usually 1:0.1 to 10, preferably 1:0.5 to 5, a treating temperature is usually 25° to 60° C., preferably 40° to 60° C., and a treating time is usually 5 to 120 minutes, preferably 30 to 90 minutes.

Removal of the catalyst components can be performed at any desired stage after oligomerization. Therefore, the reaction mixture containing the catalyst components is not limited to the reaction mixture which has just been led out of the reaction system, and it may be the reaction mixture from which the main components of α-olefin oligomers and/or solvent have been distilled away. However, in case the catalyst components are removed from the reaction mixture from which the great part of α-olefin oligomers and solvent has been distilled away, there may arise the problems such as deposition of the catalyst components on the distillation column in the distillation separation immediately before the removal operation. Therefore, removal of the catalyst components needs to be conducted at a stage where the catalyst components are not yet concentrated to a high degree after distillation of the reaction mixture.

Metal ions in the acidic or alkaline aqueous solution after extraction treatment can be recovered by a known method, for example, a method using a chelate resin. "Diaion CR10", "Diaion CR11" (produced by Mitsubishi Kasei Corporation), can be used as chelate resin. These chelate resins enable efficient recovery of trivalent chromium ions and aluminum ions. For recovering metal ions, it is also possible to employ a method in which the desired substances are precipitated as insoluble metals by making use of a pertinent chemical reaction, or a combination of such method and the method using a chelate resin.

The reaction mixture cleared of the catalyst components is usually washed with water to remove the acid or alkali mixed therein and then separated into α-olefin oligomers and solvent by distillation. Such distillation separation can be accomplished by using a known distillation apparatus. The recovered solvent may be recycled to the reaction system.

In the present invention, other α-olefin oligomers than 1-hexene, for example, 1-heptene and 1-octene can also be produced in a relatively high yield. That is, according to the present invention, it is possible to produce α-olefin oligomers having (n+4) carbon atoms by carrying out oligomerization of ethylene and an α-olefin having n carbon atoms (wherein n is an integer of not less than 3). In producing α-olefin oligomers having not less than 7 carbon atoms according to the said method, α-olefin and chromium-based catalyst are contacted with each other in a contacting mode where chromium compound and alkylaluminum compound are inhibited from previously contacting with each other. Here, the term "α-olefin" is used to refer to both ethylene and α-olefin having n carbon atoms. However, when utilizing ethylene and/or α-olefin having n carbon atoms as reaction solvent, one of them may be previously introduced into the reactor.

As α-olefin having n carbon atoms, there can be used substituted or non-substituted α-olefins having 3 to 30 carbon atoms, such as propylene, 1-butene, 1-hexene, 1-octene, 3-methyl-1-butene, 4-methyl-1-pentene, etc. In the present invention, the reaction (trimerization reaction) of 2 moles of ethylene and one mole of α-olefin having n carbon atoms is carried out selectively, so that the ratio of the said α-olefin to ethylene is not specifically defined. Actually, 0.01 to 1,000 moles of α-olefin having n carbon atoms is used to one mole of ethylene, and an appropriate ratio is selected from this range so that a product having the desired compositional distribution will be obtained.

The α-olefin oligomers preparation process of the present invention is especially advantageous, in the following points (i) to (iii), for industrial production of 1-hexene.

(i) The process is capable of producing 1-hexene from ethylene with high selectivity and in a high yield.

(ii) Oligomerization reaction of ethylene is carried out in a solvent having higher boiling point than 1-hexene, followed by degassing to reduce the pressure to not more than 3 kg/cm$^2$(G), and then the by-products are separated, so that separation of the by-products is easy to perform. As the reaction solvent having higher boiling point than 1-hexene, chain or alicyclic saturated hydrocarbons such as hexane, heptane, octane, cyclohexane, methylcyclohexane, decalin, etc., aromatic hydrocarbons such as benzene, toluene, xylene, ethylbenzene, mesitylene, tetralin, etc.; chlorinated chain hydrocarbons such as carbon tetrachloride, dichloroethane, trichloroethane, tetrachloroethane, etc.; and chlorinated aromatic hydrocarbons such as chlorobenzene, dichlorobenzene, etc.; can be used.

Oligomerization of α-olefin such as ethylene is usually carried out under pressure, and ensuing separation of the by-products is performed with the pressure in the reaction being substantially maintained unchanged. This is because of the following reason. In production of 1-hexene according to the conventional method, the yield of 1-hexene is unsatisfactory and, under certain reaction conditions, low-boiling point substance (1-butene) is produced as by-products in large quantity (about not less than 15 wt %). Accordingly, when pressure is reduced close to ordinary pressure after the reaction, the cooling load necessary for distillation separation of 1-butene (boiling point: −6.47° C.) from the unreacted ethylene is increased. According to the conventional method, therefore, it is essential to perform separation of the by-products without reducing pressure after the reaction and then separate 1-butene by distillation, with the pressure being gradually reduced in the ensuing unit operations. However, separation of the by-product polymers under pressure not only necessitates a specific solid/liquid separating device but is also poor in operating efficiency, and in some cases, it may invite additional disadvantages such as blocking of the solid/ liquid separator by the by-product polymers. On the other hand, when 1-hexene is produced according to the α-olefin oligomers production process of the present invention, since 1-hexene can be obtained in a high yield while suppressing formation of the by-product such as 1-butene, there is no absolute need for recovering 1-butene, and when it is this by-product by distillation under ordinary pressure, the cooling load necessary for distillation separation can be lessened remarkably. According to the present invention, the content (the amount produced as by-product) of 1-butene in the α-olefin oligomer composition can be reduced to not more than 10 wt %, while the content of 1-hexene therein can be increased to not less than 70 wt %, or even to not less than 85 wt %.

According to the present invention, by-product polymers can be separated after reducing the pressure to not more than 3 kg/cm²(G) by degassing after the reaction. When the pressure is reduced to not more than 3 kg/cm²(G), use of a relatively simple solid/liquid separator is possible, and also there is little possibility of the solid/liquid separator being blocked by the by-product polymers. It is, however, preferable to reduce the pressure to not more than 1.9 kg/cm²(G) which is specified by law as limit pressure of second class high pressure vessel. It is even more preferable to reduce the pressure to not more than 0.2 kg/cm²(G), under which it is possible to perform substantially the same operations as under ordinary pressure.

(iii) Since the load of distillation separation of the reaction solvent is small, the benefit of recycling of the solvent is large. When the obtained reaction product composition contains a large number of the substances which are hard to separate from each other, the benefit of recycling the reaction solvent is lessened because of large load of distillation separation of the reaction solvent. In contrast, when 1-hexene is produced according to the α-olefin oligomers production process of the present invention, the content of 1-hexene in the obtained α-olefin oligomer composition is at least 50 wt %, and it can be increased to not less than 75 wt %, or even to not less than 85 wt %. Distillation separation of 1-hexene and reaction solvent can be accomplished by using a known type of distillation apparatus. Distillation operation may be either batchwise or continuous. In either case, 1-hexene is usually distilled out from top of the distillation tower. The reaction solvent recovered as bottom product contains other α-olefins than 1-hexene, but their content is small. In the present invention, therefore, the reaction solvent recovered in the course of distillation separation of 1-hexene can be recycled in the form as it is to the reaction system during the period until the content of other α-olefins than 1-hexene in the reaction system reaches a prescribed concentration. Also, part of the reaction solvent containing such α-olefins may be recycled to the reaction system. It is of course possible to recycle the whole amount of the reaction solvent recovered in distillation separation of other α-olefins than 1-hexene. In this case, distillation separation can be accomplished in the same way as described above, but the distillation load is greatly lessened because of small content of said α-olefins in the reaction solvent.

According to the present invention, there is further provided a novel α-olefin oligomer composition which is a reaction product composition obtained from oligomerization reaction of α-olefins, comprising not less than 85% by weight of 1-hexene and not more than 15% by weight of the oligomers having not less than 10 carbon atoms and/or polymers.

α-Olefin oligomers useful as various types of starting material have been obtained from oligomerization reaction of α-olefins. The reaction product compositions obtained from oligomerization reaction of α-olefins, especially the compositions in which the content of 1-hexene is not less than 85% by weight are of high industrial utility, and above all, the compositions with a 1-hexene content of not less than 90% by weight are of particularly high industrial value.

In much of the reaction product compositions (α-olefin oligomer compositions) obtained according to the conventional methods, the content of the oligomers having 4 to 8 carbon atoms is not more than 75 wt %, that is, such compositions contain the polymers of various carbon atoms beside the above-mentioned. When, for example, the oligomer having 4 carbon atoms is represented by "C4", a typical example of composition confirmed in a follow-up test by the present inventors is as follows:

C4: 19%; C6: 40%; C8: 16%; C10: 13%;

C12: 7%; C14: 3%; C16: 1%; C18: 1%

In the case of this reaction product composition, since there are contained many substances which are hard to separate from each other because of their close boiling points and also the content of the oligomers having 4 to 8 carbon atoms is small, the fractionating operation is difficult to carry out and also the load of the fractionating process is large.

The α-olefin oligomer compositions provided according to the present invention are rich with the oligomers having 4 to 8 carbon atoms, so that the load of the fractionating process is small and, therefore, the compositions are usable as various types of starting material to industrial advantage. The compositions are particularly suited for use as starting material for L-LDPE which is a very useful resin, and they can even be used in the form as they are as starting material for the preparation of L-LDPE with certain specific properties. In the preferred α-olefin oligomer compositions of the present invention, the content of 1-hexene is not less than 85 wt %. In the more preferred α-olefin oligomer compositions of the present invention, the content of 1-hexene is not less than 90 wt % and the each content of the origomers and/or polymers having not less than 12 carbon atoms is usually 1 to 2 wt % or less. These α-olefin oligomer compositions of the present invention can be obtained by removing the starting α-olefins after oligomerization reaction thereof.

According to the present invention described above, oligomers of α-olefins such as 1-hexene can be produced in a high yield with high selectivity without complicate operations and in an industrially advantageous way. It is also possible to prevent deposition of the by-product polymers on the reactor, distillation column, other incidental equipment, and piping. Separation of the by-product polymers is easy and a significant reduction of solvent cost is realized. Further, according to the present invention, purification of α-olefin oligomers to a very high degree can be attained. Still further, according to the present invention, since it is possible to obtain 1-hexene in a high yield, distillation recovery of the reaction solvent to be recycled to the reaction system can be practiced at low load, and separation of the by-product polymers after the reaction can be accomplished under ordinary pressure or low pressure in an industrially advantageous way. Moreover, according to the present invention, there are provided α-olefin oligomer compositions which are reaction product compositions obtained from oligomerization reaction of α-olefins and which are rich with the oligomers having 4 to 8 carbon atoms, therefore

21 require small load for fractionation and hence α-olefin oligomer compositions can be offered as various types of starting material to industrial advantage.

EXAMPLES

The present invention is explained in more detail in the following Examples and Comparative Examples; however, it should be recognized that these examples are presented for illustrative purposes only and should not be construed as limiting the scope of the invention.

Example 1

A 300 ml autoclave dried by a dryer at 150° C. was assembled in a hot state and then the atmosphere in the autoclave was replaced with nitrogen in vacuum. A catalyst feed pipe equipped with a rupture plate was previously attached to the autoclave. n-Heptane (45 ml), a n-heptane solution of pyrrole (0.030 mmol) and a n-heptane solution of triethylaluminum (0.800 mmol) were charged to the autoclave, while a n-heptane solution of chromium (III) acetylacetonate (10 mg, 0.029 mmol) was charged to the catalyst feed pipe. The total amount of n-heptane was 50 ml.

First, the autoclave was heated to a temperature of 100° C. and then ethylene was introduced thereinto from the catalyst feed pipe at a temperature of 100° C. The rupture plate was ruptured under ethylene pressure and a chromium compound was introduced into the barrel of the autoclave to start oligomerization of ethylene. Ethylene was introduced until the overall pressure reached 35 kg/cm²(G), and thereafter the overall pressure was kept at 35 kg/cm²(G), while maintaining the temperature at 100° C. One hour later, ethanol was injected into the reaction mixture to terminate the reaction.

After releasing ethylene from the autoclave, the by-product polymers (mostly polyethylene) in the reaction mixture were separated by filtration to obtain α-olefin oligomers. The results of compositional analysis of this α-olefin oligomers by gas chromatography are shown along with other data in Table 1.

Examples 2–12

The same procedure as in Example 1 was carried out except that the operating conditions shown in Tables 1–3 were employed. In Example 12, however, 2,5-dimethylpyrrole was used in place of pyrrole. The results are shown in Tables 1–3.

Example 13

The same procedure as in Example 1 was conducted except for a change of the contacting mode between ethylene and chromium-based catalyst, that is, a n-heptane solution of chromium (III) (2-ethylhexanoate) (10 mg, 0.021 mmol) and a n-heptane solution of 2,5-dimethylpyrrole (0.065 mmol) were charged to the autoclave while a n-heptane solution of triethylaluminum (0.400 mmol) was charged to the catalyst feed pipe. The total amount of n-heptane was 50 ml. The results are shown in Table 4.

Examples 14–17

The same procedure as in Example 1 was conducted except that a 2.4-liter autoclave was used for enlarging the scale of reaction. The results are shown in Tables 4 and 5.

Comparative Example 1

A 300 ml autoclave dried by a 150° C. dryer was assembled in a hot state and then the atmosphere in the autoclave was replaced with nitrogen in vacuum. A catalyst feed pipe equipped with a rupture plate was previously attached to this autoclave. n-Heptane (44 ml), a n-heptane solution of chromium (III) 2-ethylhexanoate (10 mg, 0.021 mmol) and a n-heptane solution of triethylaluminum (0.400 mmol) were charged to the autoclave, while a n-heptane solution of 2,5-dimethylpyrrole (0.0650 mmol) was charged to the catalyst feed pipe. The total amount of n-heptane was 50 ml.

First, the autoclave was heated to 100° C. and then ethylene was introduced thereinto from the catalyst feed pipe at a temperature of 100° C. The rupture plate was ruptured under ethylene pressure to introduce 2,5-dimethylpyrrole into the barrel of the autoclave to start oligomerization of ethylene. Ethylene was introduced until the overall pressure reached 35 kg/cm²(G). Thereafter the overall pressure was kept at 35 kg/cm²(G), while maintaining the temperature at 100° C. One hour later, ethanol was injected in the reaction mixture to terminate the reaction. After conducting the same operations as in Example 1, α-olefin oligomers were obtained. The results of gas chromatographic analysis of the obtained α-olefin oligomers are shown along with other data in Table 5.

Comparative Example 2

Preparation of Cr compound A 15 ml of tetrahydrofuran (THF) was added to 0.815 g (20.3 mmol) of NaH, and to the resultant solution was added dropwise 1.4 ml (20 mmol) of pyrrole dissolved in 5 ml of THF. After stirring at room temperature for one hour, the resulting solution was added dropwise to 1.23 g (10 mmol) of $CrCl_2$ suspended in 20 ml of THF. Thereafter 5 ml of THF was added and the resultant mixture was heated under reflux for 20 hours. The precipitate was filtered off, 100 ml of pentane was added to the filtrate and the mixture was left still at a temperature of 5° C. The produced precipitate was collected by filtration and dried to obtain 0.506 g of a dark green powder. The contents of the component elements in this powder were as follows:

Cr: 19.1%; C: 52.3%; H: 5.45%; N: 11.6%.

A 300 ml autoclave dried by a dryer at 150° C. was assembled in a hot state and then the atmosphere in the autoclave was replaced with nitrogen in vacuum. To this autoclave were charged n-heptane (44 ml), a n-heptane solution of triethylaluminum (0.120 mmol) and a heptane suspension of Cr compound A (10 mg). The total amount of n-heptane was 50 ml. The resultant mixture was treated at a temperature of 90° C. for 30 minutes and then ethylene was introduced at a temperature of 90° C. After this, the overall pressure was kept at 35 kg/cm²(G) while maintaining the temperature at 100° C. 0.5 hour later, ethanol was injected into the autoclave to terminate the reaction. Thereafter, the same operations as in Example 1 were repeated to recover α-olefin oligomers. The results of gas chromatographic analysis of the α-olefin oligomers are shown along with other data in Table 5.

In the tables shown below, the following abbreviations are used:

HP: n-heptane

CHX: cyclohexane

Cr-1: chromium (III) acetylacetonate

Cr-2: chromium (III) (2,2,6,6-tetramethyl-3,5-heptanedionate)

Cr-3: chromium (III) 2-ethylhexanoate

Cr-4: CrCl₃3-pyridine
Cr-5: (CO)₅Cr (=CCH₃(OCH₃))
Cr-A: chromium compound synthesized in Comparative Example 2

Also, in the following tables, "contact method A" is a method in which α-olefin and chromium compound are introduced into a solution containing an amine (pyrrole) and an alkylaluminum compound; "contact method B" is a method in which α-olefin and alkylaluminum compound are introduced into a solution containing a chromium compound and an amine (pyrrole); and "contact method X" is a method in which chromium compound and alkylaluminum compound are first heat-treated and then contacted with α-olefin. The unit of catalyst efficiency is "g- α-olefin/1 g-chromium compound", and the unit of catalyst activity is "g- α-olefin/1 g-chromium·hr".

TABLE 1

|  | Example | | | |
|---|---|---|---|---|
|  | 1 | 2 | 3 | 4 |
| Kind of solvent (amount: ml) | HP(50) | HP(50) | HP(50) | HP(50) |
| Kind of Cr compound | Cr-1 | Cr-1 | Cr-1 | Cr-1 |
| Amount of Cr compound (mg) | 10 | 10 | 10 | 10 |
| Molar amount of Cr compound (mmol) (a) | 0.029 | 0.029 | 0.029 | 0.029 |
| Molar amount of pyrrole (mmol) (b) | 0.030 | 0.060 | 0.090 | 0.050 |
| Molar amount of Et₃Al (mmol) (c) | 0.800 | 0.800 | 0.800 | 0.800 |
| Molar ratio of catalyst components (a:b:c) | 1:1:28 | 1:2:28 | 1:3:28 | 1:2:14 |
| Reaction temperature (°C.) | 100 | 100 | 100 | 100 |
| Ethylene pressure (kg/cm²) | 35 | 35 | 35 | 35 |
| Reaction time (Hr) | 1.0 | 1.0 | 1.0 | 1.0 |
| Contacting method | A | A | A | A |
| <Product yield (g)> | 16.0 | 15.4 | 14.7 | 14.2 |
| <Compositional distribution (wt %)> | | | | |
| $C_4$ | 6.4 | 6.0 | 6.2 | 4.8 |
| $C_6$ (total) | 45.6 | 45.7 | 48.4 | 47.3 |
| 1-hexane content in $C_6$ (wt %) | 94.5 | 94.5 | 93.6 | 94.3 |
| $C_8$ | 8.2 | 7.7 | 7.1 | 5.3 |
| $C_{10-20}$ | 26.0 | 27.8 | 22.5 | 17.8 |
| $C_{22-30}$ | 6.3 | 6.8 | 6.6 | 6.5 |
| Wax | 2.7 | 2.8 | 3.8 | 12.4 |
| Polyethylene (by-product) | 4.8 | 3.3 | 5.5 | 5.9 |
| <Catalytic efficiency> | 1597 | 1543 | 1467 | 1416 |
| <Catalytic activity> | 10740 | 10380 | 9860 | 9520 |

TABLE 2

|  | Example | | | |
|---|---|---|---|---|
|  | 5 | 6 | 7 | 8 |
| Kind of solvent (amount: ml) | HP(50) | HP(50) | HP(50) | CHX(50) |
| Kind of Cr compound | Cr-2 | Cr-3 | Cr-3 | Cr-3 |
| Amount of Cr compound (mg) | 10 | 10 | 10 | 10 |
| Molar amount of Cr compound (mmol) (a) | 0.017 | 0.021 | 0.021 | 0.021 |
| Molar amount of pyrrole (mmol) (b) | 0.050 | 0.050 | 0.065 | 0.065 |
| Molar amount of Et₃Al (mmol) (c) | 0.400 | 0.400 | 0.400 | 0.400 |
| Molar ratio of catalyst components (a:b:c) | 1:3:24 | 1:2:19 | 1:3:19 | 1:3:19 |
| Reaction temperature (°C.) | 100 | 100 | 100 | 100 |
| Ethylene pressure (kg/cm²) | 35 | 35 | 35 | 35 |
| Reaction time (Hr) | 1.0 | 1.0 | 1.0 | 1.0 |
| Contacting method | A | A | A | A |
| <Product yield (g)> | 9.8 | 6.5 | 7.3 | 11.9 |
| <Compositional distribution (wt %)> | | | | |
| $C_4$ | 10.6 | 9.5 | 10.5 | 16.3 |
| $C_6$ (total) | 58.8 | 68.7 | 61.0 | 50.0 |
| 1-hexane content in $C_6$ (wt %) | 92.0 | 92.4 | 92.6 | 92.1 |
| $C_8$ | 8.8 | 6.9 | 8.0 | 11.2 |
| $C_{10-20}$ | 20.5 | 13.2 | 19.7 | 21.8 |
| $C_{22-30}$ | 1.0 | 0.7 | 0.8 | 0.5 |
| Wax | 0.1 | 0.0 | 0.1 | 0.0 |
| Polyethylene (by-product) | 0.3 | 1.0 | 0.8 | 0.2 |
| <Catalytic efficiency> | 979 | 646 | 734 | 1187 |
| <Catalytic activity> | 11350 | 6000 | 3790 | 10990 |

TABLE 3

|  | Example | | | |
|---|---|---|---|---|
|  | 9 | 10 | 11 | 12 |
| Kind of solvent (amount: ml) | HP(50) | HP(50) | HP(50) | HP(50) |
| Kind of Cr compound | Cr-3 | Cr-4 | Cr-5 | Cr-3 |
| Amount of Cr compound (mg) | 10 | 10 | 5 | 10 |
| Cr compound (mmol) (a) | 0.021 | 0.025 | 0.020 | 0.021 |
| Pyrrole (mmol) (b) | 0.065 | 0.075 | 0.060 | 0.065 |
| Et₃Al (mmol) (c) | 4.160 | 0.510 | 0.400 | 0.400 |
| Molar ratio of catalyst components (a:b:c) | 1:3:198 | 1:3:20 | 1:3:20 | 1:3:19 |
| Reaction temperature (°C.) | 100 | 100 | 60 | 100 |
| Ethylene pressure (kg/cm²) | 35 | 35 | 35 | 35 |
| Reaction time (Hr) | 1.0 | 1.0 | 1.0 | 1.0 |
| Contacting method | A | A | A | A |
| <Product yield (g)> | 13.3 | 7.4 | 1.9 | 27.0 |
| <Compositional distribution (wt %)> | | | | |
| $C_4$ | 13.2 | 4.9 | 8.0 | 10.0 |
| $C_6$ (total) | 66.6 | 71.5 | 81.2 | 60.4 |
| 1-hexane content in $C_6$ (wt %) | 93.1 | 92.9 | 94.5 | 90.1 |
| $C_8$ | 7.8 | 5.0 | 3.8 | 6.0 |
| $C_{10-20}$ | 11.8 | 16.4 | 7.0 | 23.6 |
| $C_{22-30}$ | 0.1 | 0.8 | 0.0 | 0.0 |
| Wax | 0.0 | 0.1 | 0.0 | 0.0 |

TABLE 3-continued

| | Example | | | |
|---|---|---|---|---|
| | 9 | 10 | 11 | 12 |
| Polyethylene (by-product) | 0.5 | 1.4 | 0.0 | 0.0 |
| <Catalytic efficiency> | 1332 | 744 | 388 | 2695 |
| <Catalytic activity> | 12330 | 5680 | 1868 | 25000 |

TABLE 4

| | Example | | | |
|---|---|---|---|---|
| | 13 | 14 | 15 | 16 |
| Kind of solvent (amount: ml) | HP(50) | HP(1000) | HP(1000) | HP(1000) |
| Kind of Cr compound | Cr-3 | Cr-3 | Cr-3 | Cr-3 |
| Amount of Cr compound (mg) | 10 | 200 | 200 | 200 |
| Cr compound (mmol) (a) | 0.021 | 0.420 | 0.420 | 0.420 |
| Pyrrole (mmol) (b) | 0.065 | 1.244 | 1.244 | 1.244 |
| Et$_3$Al (mmol) (c) | 0.400 | 2.000 | 2.000 | 2.000 |
| Molar ratio of catalyst components (a:b:c) | 1:3:19 | 1:3:5 | 1:3:5 | 1:3:5 |
| Reaction temperature (° C.) | 100 | 60 | 40 | 30 |
| Ethylene pressure (kg/cm$^2$) | 35 | 35 | 35 | 35 |
| Reaction time (Hr) | 1.0 | 1.0 | 1.0 | 1.0 |
| Contacting method | B | A | A | A |
| <Product yield (g)> | 32.5 | 57.4 | 41.8 | 45.2 |
| <Compositional distribution (wt %)> | | | | |
| C$_4$ | 2.0 | 2.7 | 3.0 | 4.1 |
| C$_6$ (total) | 71.9 | 90.2 | 92.1 | 89.3 |
| 1-hexane content in C$_6$ (wt %) | 92.7 | 99.2 | 99.5 | 99.4 |
| C$_8$ | 1.7 | 2.5 | 2.7 | 3.5 |
| C$_{10-20}$ | 18.6 | 4.3 | 1.4 | 1.9 |
| C$_{22-30}$ | 5.8 | 0.1 | 0.0 | 0.0 |
| Wax | 0.0 | 0.0 | 0.0 | 0.0 |
| Polyethylene (by-product) | 0.0 | 0.4 | 0.7 | 1.0 |
| <Catalytic efficiency> | 3252 | 287 | 209 | 226 |
| <Catalytic activity> | 30100 | 2758 | 2012 | 2174 |

TABLE 5

| | Example | Comparative Example | |
|---|---|---|---|
| | 17 | 1 | 2 |
| Kind of solvent (amount: ml) | HP(50) | HP(50) | HP(50) |
| Kind of Cr compound | Cr-3 | Cr-3 | Cr-A |
| Amount of Cr compound (mg) | 200 | 10 | 10 |
| Cr compound (mmol) (a) | 0.420 | 0.021 | — |
| Pyrrole (mmol) (b) | 1.659 | 0.065 | — |
| Et$_3$Al (mmol) (c) | 2.000 | 0.400 | 0.120 |
| Molar ratio of catalyst components (a:b:c) | 1:4:5 | 1:3:19 | — |
| Reaction temperature (° C.) | 60 | 10 | 100 |
| Ethylene pressure (kg/cm$^2$) | 35 | 35 | 35 |
| Reaction time (Hr) | 1.0 | 1.0 | 1.0 |
| Contacting method | A | X | X |
| <Product yield (g)> | 41.5 | 0.8 | 0.6 |
| <Compositional distribution (wt %)> | | | |
| C$_4$ | 1.4 | 0.8 | 0.6 |
| C$_6$ (total) | 92.3 | 85.3 | 78.7 |
| 1-hexane content in C$_6$ (wt %) | 99.6 | 90.6 | 85.0 |
| C$_8$ | 2.1 | 1.6 | tr. |
| C$_{10-20}$ | 3.5 | 8.1 | tr. |
| C$_{22-30}$ | 0.2 | 0.4 | 0.0 |
| Wax | 0.0 | 0.0 | 0.0 |
| Polyethylene (by-product) | 0.4 | 1.1 | 5.1 |
| <Catalytic efficiency> | 208 | 80 | 60 |
| <Catalytic activity> | 1997 | 739 | 628 |

Example 18

There was used a tubular reactor having a pressure coiled pipe of 6 mm in inner diameter and 10.5 m in length, which is disposed inside the jacket, and a catalyst feed pipe connected to a point 0.5 m from the front end of said coiled tubular. The atmosphere of the pipe reactor was replaced with nitrogen in vacuum and then the interior temperature of the jacket was kept at 100° C.

n-Heptane, a n-heptane solution of pyrrole (0.017 mmol/ml) and a n-heptane solution of triethylaluminum (0.453 mmol/ml) were introduced continuously from the front end of the said tubular reactor at the rates of 253 ml/hr, 10 ml/hr and 10 ml/hr, respectively, while a n-heptane solution of chromium (III) acetylacetonate (5.6 mg, 0.0164 mmol/ml) was introduced continuously together with ethylene (100° C.) from the catalyst feed pipe at a rate of 10 ml/hr. Reaction pressure was adjusted to 35 kg/cm$^2$ by ethylene pressure. Introduction time of the respective components was controlled so that retention time would become one hour. The reaction mixture effusing from the tubular reactor was introduced into a pressure vessel separately provided in connection to the tubular reactor. Ethanol was injected into the reaction mixture in the pressure vessel to terminate the reaction.

After releasing pressure from the vessel, the by-product polymers (mostly polyethylene) in the reaction mixture were separated by filtration to obtain α-olefin oligomers. The results of compositional analysis of the obtained α-olefin oligomers by gas chromatography are shown along with other data in Table 6.

Examples 19–29

The same procedure as in Example 18 was carried out except that the reaction conditions shown in Tables 6–8 were employed. In Example 29, however, 2,5-dimethylpyrrole was used in place of pyrrole. The results are shown in Tables 5–8.

Example 30

The same procedure as in Example 18 was conducted except for a change of the contacting mode between ethylene and chromium-based catalyst, that is, n-heptane, a n-heptane solution of chromium (III) (2-ethylhexanoate) (107.6 mg, 0.226 mmol/ml) and a n-heptane solution of 2,5-dimethylpyrrole (0.012 mmol/ml) were introduced continuously from the front end of the tubular reactor at the rates of 253 ml/hr, 10 ml/hr and 10 ml/hr, respectively, while a heptane solution of triethylaluminum (0.037 mmol/ml) was introduced continuously together with ethylene (100° C.) from the catalyst feed pipe at a rate of 10 ml/hr. The results are shown in Table 9.

Examples 31–34

There was used as reactor a multi-stage mixing tank having 2 sets of 2.4 liter (1 liter in fluid capacity) autoclave arranged in series to each other and connected by an overflow pipe. Each of the autoclaves, after dried by a dryer at 150° C., was assembled in a hot state and then the atmosphere in each said autoclave was replaced with nitrogen in vacuum. n-Heptane, a n-heptane solution of pyrrole (0.124 mmol/ml) and a n-heptane solution of triethylaluminum (0.200 mmol/ml) were introduced continuously into the first autoclave at the rates of 970 ml/hr, 10 ml/hr and 10 ml/hr, respectively, and the obtained mixed solution was overflowed to the second autoclave. At the same time, a n-heptane solution of chromium (III) acetylacetonate (14 mg, 0.042 mmol/ml) was introduced continuously together with ethylene into the second autoclave at a rate of 10 ml/hr. As for the reaction conditions, those shown in Tables 4 and 5 were employed. Reaction pressure was adjusted with ethylene pressure, and retention time was controlled by the introduction rates of the feedstocks. The reaction mixture effusing from the overflow pipe of the second autoclave was introduced into a pressure vessel provided separately in connection to the overflow pipe. Ethanol was injected into the reaction mixture in the pressure vessel to terminate the reaction.

After releasing pressure from the vessel, the by-product polymers (mostly polyethylene) in the reaction mixture were separated by filtration to obtain α-olefin oligomers. The results of compositional analysis of the α-olefin oligomers are shown along with other data in Tables 9 and 10.

TABLE 6

| | Example | | | |
|---|---|---|---|---|
| | 18 | 19 | 20 | 21 |
| Kind of solvent | HP | HP | HP | HP |
| Kind of Cr compound | Cr-1 | Cr-1 | Cr-1 | Cr-1 |
| Amount of Cr compound (mg/hour) | 56 | 56 | 56 | 56 |
| Molar amount of Cr compound (mmol/hour) (a) | 0.164 | 0.164 | 0.164 | 0.164 |
| Molar amount of pyrrole (mmol/hour) (b) | 0.170 | 0.340 | 0.510 | 0.283 |
| Molar amount of Et$_3$Al (mmol/hour) (c) | 4.530 | 4.530 | 4.530 | 2.260 |
| Molar ratio of catalyst components (a:b:c) | 1:1:28 | 1:2:28 | 1:3:28 | 1:2:14 |
| Reaction temperature (° C.) | 100 | 100 | 100 | 100 |
| Ethylene pressure (kg/cm$^2$) | 35 | 35 | 35 | 35 |
| Reaction time (Hr) | 1.0 | 1.0 | 1.0 | 1.0 |
| Contacting method | A | A | A | A |
| <Product yield (g)> | 90.6 | 87.2 | 83.2 | 80.4 |

TABLE 6-continued

| | Example | | | |
|---|---|---|---|---|
| | 18 | 19 | 20 | 21 |
| <Compositional distribution (wt %)> | | | | |
| C$_4$ | 6.0 | 6.3 | 6.0 | 4.5 |
| C$_6$ (total) | 45.8 | 45.2 | 48.6 | 47.6 |
| 1-hexane content in C$_6$ (wt %) | 94.7 | 94.2 | 93.3 | 94.3 |
| C$_8$ | 8.0 | 7.8 | 7.3 | 5.5 |
| C$_{10-20}$ | 26.2 | 27.9 | 22.3 | 17.7 |
| C$_{22-30}$ | 6.5 | 6.7 | 6.7 | 6.4 |
| Wax | 2.6 | 2.9 | 3.4 | 12.7 |
| Polyethylene (by-product) | 4.9 | 3.2 | 5.7 | 5.6 |
| <Catalytic efficiency> | 1595 | 1546 | 1465 | 1419 |
| <Catalytic activity> | 10743 | 10382 | 9863 | 9526 |

TABLE 7

| | Example | | | |
|---|---|---|---|---|
| | 21 | 23 | 24 | 25 |
| Kind of solvent | HP | HP | HP | CHX |
| Kind of Cr compound | Cr-2 | Cr-3 | Cr-3 | Cr-3 |
| Amount of Cr compound (mg/hour) | 5.6 | 5.7 | 5.7 | 5.7 |
| Molar amount of Cr compound (mmol/hour) (a) | 0.096 | 0.119 | 0.119 | 0.119 |
| Molar amount of pyrrole (mmol/hour) (b) | 0.283 | 0.283 | 0.368 | 0.368 |
| Molar amount of Et$_3$Al (mmol/Hr) (c) | 2.260 | 2.260 | 2.260 | 2.260 |
| Molar ratio of catalyst components (a:b:c) | 1:3:24 | 1:2:19 | 1:3:19 | 1:3:19 |
| Reaction temperature (° C.) | 100 | 100 | 100 | 100 |
| Ethylene pressure (kg/cm$^2$) | 35 | 35 | 35 | 35 |
| Reaction time (Hr) | 1.0 | 1.0 | 1.0 | 1.0 |
| Contacting method | A | A | A | A |
| <Product yield (g)> | 55.5 | 36.8 | 41.3 | 67.4 |
| <Compositional distribution (wt %)> | | | | |
| C$_4$ | 10.8 | 9.0 | 10.1 | 16.5 |
| C$_6$ (total) | 58.6 | 68.7 | 61.4 | 50.0 |
| 1-hexane content in C$_6$ (wt %) | 92.2 | 92.6 | 92.5 | 92.4 |
| C$_8$ | 8.8 | 7.0 | 8.2 | 11.4 |
| C$_{10-20}$ | 20.4 | 13.4 | 19.5 | 21.8 |
| C$_{22-30}$ | 1.0 | 0.9 | 0.8 | 0.4 |
| Wax | 0.1 | 0.0 | 0.1 | 0.1 |
| Polyethylene (by-product) | 0.3 | 1.0 | 0.8 | 0.2 |
| <Catalytic efficiency> | 976 | 648 | 736 | 1189 |
| <Catalytic activity> | 11355 | 6005 | 6793 | 10995 |

TABLE 8

| | Example | | | |
|---|---|---|---|---|
| | 26 | 27 | 28 | 29 |
| Kind of solvent | HP | HP | HP | HP |
| Kind of Cr compound | Cr-3 | Cr-4 | Cr-5 | Cr-3 |
| Amount of Cr compound (mg/hour) | 5.7 | 5.7 | 5.7 | 5.7 |

TABLE 8-continued

| | Example | | | |
|---|---|---|---|---|
| | 26 | 27 | 28 | 29 |
| Molar amount of Cr compound (mmol/hour) (a) | 0.119 | 0.142 | 0.113 | 0.119 |
| Molar amount of pyrrole (mmol/hour) (b) | 0.368 | 0.425 | 0.340 | 0.368 |
| Molar amount of Et$_3$Al (mmol/hour) (c) | 23.50 | 2.890 | 2.260 | 2.260 |
| Molar ratio of catalyst components (a:b:c) | 1:3:198 | 1:3:20 | 1:3:20 | 1:3:19 |
| Reaction temperature (°C.) | 100 | 100 | 60 | 100 |
| Ethylene pressure (kg/cm$^2$) | 35 | 35 | 35 | 35 |
| Reaction time (Hr) | 1.0 | 1.0 | 1.0 | 1.0 |
| Contacting method | A | A | A | A |
| <Product yield (g/hour)> | 75.3 | 41.9 | 10.7 | 152.8 |
| <Compositional distribution (wt %)> | | | | |
| C$_4$ | 13.0 | 4.6 | 8.3 | 10.3 |
| C$_6$ (total) | 66.9 | 71.8 | 81.0 | 60.1 |
| 1-hexene content in C$_6$ (wt %) | 93.1 | 92.9 | 94.5 | 90.1 |
| C$_8$ | 7.7 | 4.9 | 3.7 | 5.8 |
| C$_{10-20}$ | 11.7 | 16.5 | 7.0 | 23.7 |
| C$_{22-30}$ | 0.1 | 0.6 | 0.0 | 0.1 |
| Wax | 0.1 | 0.1 | 0.0 | 0.0 |
| Polyethylene (by-product) | 0.5 | 1.6 | 0.1 | 0.0 |
| <Catalytic efficiency> | 1335 | 742 | 387 | 2690 |
| <Catalytic activity> | 12335 | 5683 | 1869 | 25019 |

TABLE 9

| | Example | | | |
|---|---|---|---|---|
| | 30 | 31 | 32 | 33 |
| Kind of solvent | HP | HP | HP | HP |
| Kind of Cr compound | Cr-3 | Cr-3 | Cr-3 | Cr-3 |
| Amount of Cr compound (mg/hour) | 5.7 | 200 | 200 | 200 |
| Molar amount of Cr compound (mmol/hour) (a) | 0.119 | 0.042 | 0.420 | 0.420 |
| Molar amount of pyrrole (mmol/hour) (b) | 0.368 | 1.244 | 1.244 | 1.244 |
| Molar amount of Et$_3$Al (mmol/hour) (c) | 2.260 | 2.000 | 2.000 | 2.000 |
| Molar ratio of catalyst components (a:b:c) | 1:3:19 | 1:3:5 | 1:3:5 | 1:3:5 |
| Reaction temperature (°C.) | 100 | 60 | 40 | 30 |
| Ethylene pressure (kg/cm$^2$) | 35 | 35 | 35 | 35 |
| Reaction time (Hr) | 1.0 | 1.0 | 1.0 | 1.0 |
| Contacting method | B | A | A | A |
| <Product yield (g/hour)> | 184.0 | 57.4 | 41.8 | 45.2 |
| <Compositional distribution (wt %)> | | | | |
| C$_4$ | 2.3 | 2.4 | 3.3 | 4.5 |
| C$_6$ (total) | 71.6 | 90.5 | 92.1 | 89.0 |
| 1-hexene content in C$_6$ (wt %) | 92.7 | 99.2 | 99.5 | 99.4 |
| C$_8$ | 1.5 | 2.2 | 2.9 | 3.6 |
| C$_{10-20}$ | 18.8 | 4.6 | 1.3 | 1.8 |
| C$_{22-30}$ | 5.7 | 0.1 | 0.1 | 0.1 |
| Wax | 0.1 | 0.1 | 0.0 | 0.0 |
| Polyethylene (by-product) | 0.0 | 0.3 | 0.5 | 1.1 |
| <Catalytic efficiency> | 3250 | 285 | 211 | 220 |
| <Catalytic activity> | 30111 | 2761 | 2015 | 2176 |

TABLE 10

| | Example 34 |
|---|---|
| Kind of solvent | HP |
| Kind of Cr compound | Cr-3 |
| Amount of Cr compound (mg/hour) | 200 |
| Molar amount of Cr compound (mmol/hour) (a) | 0.420 |
| Molar amount of pyrrole (mmol/hour) (b) | 1.659 |
| Molar amount of Et$_3$Al (mmol/hour) (c) | 2.000 |
| Molar ratio of catalyst components (a:b:c) | 1:4:5 |
| Reaction temperature (°C.) | 60 |
| Ethylene pressure (kg/cm$^2$) | 35 |
| Reaction time (Hr) | 1.0 |
| Contacting method | A |
| <Product yield (g/hour)> | 41.5 |
| <Compositional distribution (wt %)> | |
| C$_4$ | 1.1 |
| C$_6$ (total) | 92.6 |
| 1-hexene content in C$_6$ (wt %) | 99.6 |
| C$_8$ | 2.5 |
| C$_{10-20}$ | 3.1 |
| C$_{22-30}$ | 0.1 |
| Wax | 0.0 |
| Polyethylene (by-product) | 0.5 |
| <Catalytic efficiency> | 213 |
| <Catalytic activity> | 2011 |

Example 35 n-Heptane (47 ml), a n-heptane solution of pyrrole (0.063 mmol), a n-heptane solution of triethylaluminum (0.400 mmol) and 1,5-cyclooctadiene (9.410 mmol) as additional component were charged to the same autoclave as used in Example 1, while a heptane solution of chromium (III) (2-ethylhexanoate) (10 mg, 0.021 mmol) was charged to the catalyst feed pipe. The total amount of n-heptane was 50 ml. Thereafter the same operations as in Example 1 were performed, and the oligomerization reaction of ethylene was conducted under the conditions shown in Table 11. The results of gas chromatographic analysis of the resultantly obtained α-olefin oligomers are shown along with other data in Table 11.

The symbol "a-1" indicating the additional component in Table 11 is 1,5-cyclooctadiene.

TABLE 11

| | Example 35 |
|---|---|
| Kind of solvent (amount: ml) | HP(50) |
| Kind of Cr compound | Cr-3 |
| Amount of Cr compound (mg/hour) | 10 |
| Molar amount of Cr compound (mmol/hour) (a) | 0.021 |
| Molar amount of pyrrole (mmol/hour) (b) | 0.063 |
| Molar amount of Et$_3$Al (mmol/hour) (c) | 0.400 |
| Molar ratio of catalyst components (a:b:c) | 1:3:19 |
| Kind of additional component | a-1 |
| Molar amount of additional substance (mmol) | 9.410 |

TABLE 11-continued

|  | Example 35 |
|---|---|
| Reaction temperature (°C.) | 100 |
| Ethylene pressure (kg/cm$^2$) | 35 |
| Reaction time (Hr) | 1.0 |
| Contact method | A |
| <Product yield (g/hour)> | 9.2 |
| <Compositional distribution (wt %)> | |
| C$_4$ | 15.1 |
| C$_6$ (total) | 52.3 |
| 1-hexene content in C$_6$ (wt %) | 95.0 |
| C$_8$ | 12.3 |
| C$_{10-20}$ | 20.1 |
| C$_{22-30}$ | 0.1 |
| Wax | 0.0 |
| Polyethylene (by-product) | 0.1 |
| <Catalytic efficiency> | 922 |
| <Catalytic activity> | 8583 |

Examples 36–39

The same procedure as in Example 35 was conducted except for a change of the additional component and employment of the reaction conditions shown in Table 12. In Example 39, mesitylene was used as additional component in place of n-heptane (47 ml). The results of gas chromatographic analysis of the obtained α-olefin oligomers are shown along with other data in Table 12.

The symbols indicating the additional components in Table 12 denote the following.

b-1: mesitylene
c-1: 1,3,5-tri-tert-butylbenzene
d-1: hexamethylbenzene

TABLE 12

|  | Example | | | |
|---|---|---|---|---|
|  | 36 | 37 | 38 | 39 |
| Kind of solvent (amount: ml) | HP(49) | HP(49) | HP(49) | HP(3) |
| Kind of Cr compound | Cr-3 | Cr-3 | Cr-3 | Cr-3 |
| Amount of Cr compound (mg/Hr) | 10 | 10 | 10 | 10 |
| Molar amount of Cr compound (mmol/hour) (a) | 0.021 | 0.021 | 0.021 | 0.021 |
| Molar amount of pyrrole (mmol/hour) (b) | 0.063 | 0.063 | 0.063 | 0.063 |
| Molar amount of Et$_3$Al (mmol/hour) (c) | 0.400 | 0.400 | 0.400 | 0.400 |
| Molar ratio of catalyst components (a:b:c) | 1:3:19 | 1:3:19 | 1:3:19 | 1:3:19 |
| Kind of additional component | b-1 | c-1 | d-1 | b-1 |
| Molar amount of additional substance (mmol) | 9.410 | 9.410 | 9.410 | 9.410 |
| Reaction temperature (°C.) | 100 | 100 | 100 | 100 |
| Ethylene pressure (kg/cm$^2$) | 35 | 35 | 35 | 35 |
| Reaction time (Hr) | 1.0 | 1.0 | 1.0 | 1.0 |
| Contact method | A | A | A | A |
| <Product yield (g/hour)> | 9.1 | 10.8 | 8.9 | 6.9 |

TABLE 12-continued

|  | Example | | | |
|---|---|---|---|---|
|  | 36 | 37 | 38 | 39 |
| <Compositional distribution (wt %)> | | | | |
| C$_4$ | 15.8 | 14.4 | 13.8 | 26.7 |
| C$_6$ (total) | 48.1 | 52.8 | 55.5 | 28.8 |
| 1-hexene content in C$_6$ (wt %) | 96.1 | 94.1 | 95.5 | 98.1 |
| C$_8$ | 13.3 | 10.9 | 10.6 | 16.8 |
| C$_{10-20}$ | 22.0 | 21.1 | 19.1 | 26.4 |
| C$_{22-30}$ | 0.5 | 0.3 | 0.6 | 0.7 |
| Wax | 0.0 | 0.0 | 0.0 | 0.0 |
| Polyethylene (by-product) | 0.2 | 0.4 | 0.4 | 0.5 |
| <Catalytic efficiency> | 910 | 1076 | 892 | 689 |
| <Catalytic activity> | 8425 | 9964 | 8258 | 6382 |

Examples 40–47

The same procedure as in Example 35 was conducted except for a change of the additional component and employment of the reaction conditions shown in Tables 13 and 14. In Example 42, toluene was not charged to the autoclave as an additional component, and 1 ml (9.41 mmol) of toluene was used for making a solution of chromium (III) (2-ethylhexanoate) and was charged to a feed pipe. In Examples 46 and 47, 2,5-dimethylpyrrole was used in place of pyrrole. The results of gas chromatographic analysis of the obtained α-olefin oligomers are shown along with other data in Tables 13 and 14.

The symbols indicating the additional components in Tables 13 and 14 denote the following.

e-1: benzene
f-1: toluene
g-1: m-xylene

TABLE 13

|  | Example | | | |
|---|---|---|---|---|
|  | 40 | 41 | 42 | 43 |
| Kind of solvent (amount: ml) | HP(50) | HP(50) | HP(50) | HP(50) |
| Kind of Cr compound | Cr-3 | Cr-3 | Cr-3 | Cr-3 |
| Amount of Cr compound (mg/hour) | 10 | 10 | 10 | 10 |
| Molar amount of Cr compound (mmol/hour) (a) | 0.021 | 0.021 | 0.021 | 0.021 |
| Molar amount of pyrrole (mmol/hour) (b) | 0.063 | 0.063 | 0.063 | 0.063 |
| Molar amount of Et$_3$Al (mmol/hour) (c) | 0.400 | 0.400 | 0.400 | 0.800 |
| Molar ratio of catalyst components (a:b:c) | 1:3:19 | 1:3:19 | 1:3:19 | 1:3:38 |
| Kind of additional component | e-1 | f-1 | f-1 | f-1 |
| Molar amount of additional substance (mmol) | 9.410 | 9.410 | 9.410 | 9.410 |
| Reaction temperature (°C.) | 100 | 100 | 100 | 100 |
| Ethylene pressure (kg/cm$^2$) | 35 | 35 | 35 | 35 |
| Reaction time (Hr) | 1.0 | 1.0 | 1.0 | 1.0 |

TABLE 13-continued

| | Example | | | |
|---|---|---|---|---|
| | 40 | 41 | 42 | 43 |
| Contact method | A | A | A | A |
| <Product yield (g/hour)> | 6.9 | 6.3 | 6.4 | 9.0 |
| $C_4$ | 18.8 | 8.3 | 22.5 | 15.0 |
| $C_6$ (total) | 47.8 | 63.0 | 49.8 | 58.2 |
| 1-hexane content in $C_6$ (wt %) | 96.1 | 96.5 | 96.7 | 96.0 |
| $C_8$ | 13.4 | 7.9 | 13.4 | 10.3 |
| $C_{10-20}$ | 19.3 | 19.1 | 13.8 | 15.4 |
| $C_{22-30}$ | 0.6 | 1.5 | 0.3 | 0.6 |
| Wax | 0.0 | 0.0 | 0.0 | 0.0 |
| Polyethylene (by-product) | 0.1 | 0.4 | 0.2 | 0.5 |
| <Catalytic efficiency> | 694 | 625 | 644 | 902 |
| <Catalytic activity> | 6430 | 5783 | 5960 | 8359 |

TABLE 14

| | Example | | | |
|---|---|---|---|---|
| | 44 | 45 | 46 | 47 |
| Kind of solvent (amount: ml) | HP(50) | HP(50) | HP(50) | HP(50) |
| Kind of Cr compound | Cr-1 | Cr-3 | Cr-3 | Cr-3 |
| Amount of Cr compound (mg/hour) | 10 | 10 | 5 | 10 |
| Molar amount of Cr compound (mmol/hour) (a) | 0.021 | 0.028 | 0.010 | 0.021 |
| Molar amount of pyrrole (mmol/hour) (b) | 0.085 | 0.063 | 0.031 | 0.063 |
| Molar amount of $Et_3Al$ (mmol/hour) (c) | 0.570 | 0.400 | 0.200 | 0.200 |
| Molar ratio of catalyst components (a:b:c) | 1:3:19 | 1:2:14 | 3:3:209 | 1:3:19 |
| Kind of additional component | f-1 | g-1 | f-1 | f-1 |
| Molar amount of additional substance (mmol) | 9.410 | 9.410 | 9.410 | 47.05 |
| Reaction temperature (°C.) | 100 | 100 | 90 | 90 |
| Ethylene pressure (kg/cm²) | 35 | 35 | 35 | 35 |
| Reaction time (Hr) | 1.0 | 1.0 | 1.0 | 1.0 |
| Contact method | A | A | A | A |
| <Product yield (g/hour)> | 9.6 | 6.0 | 4.6 | 5.2 |
| <Compositional distribution (wt %)> | | | | |
| $C_4$ | 5.1 | 18.9 | 56.8 | 57.9 |
| $C_6$ (total) | 49.4 | 48.7 | 32.1 | 29.8 |
| 1-hexane content in $C_6$ (wt %) | 94.9 | 96.3 | 96.5 | 98.3 |
| $C_8$ | 6.0 | 12.7 | 7.3 | 8.5 |
| $C_{10-20}$ | 22.6 | 18.6 | 3.5 | 3.6 |
| $C_{22-30}$ | 9.3 | 0.4 | 0.0 | 0.1 |
| Wax | 0.0 | 0.0 | 0.0 | 0.0 |
| Polyethylene (by-product) | 7.7 | 0.5 | 0.1 | 0.2 |
| <Catalytic efficiency> | 964 | 596 | 909 | 523 |
| <Catalytic activity> | 6470 | 5514 | 8420 | 4843 |

Examples 48–59

The same procedure as in Example 35 was conducted except that the additional component and employment of the reaction conditions were changed as shown in Tables 15–17. In Example 42, 1 ml (9.41 mmol) of a toluene solution of chromium (III) (2-ethylhexanoate) was charged to the autoclave as an additional component instead of toluene. In Examples 46 and 47, 2,5-dimethylpyrrole was used in place of pyrrole. The results of gas chromatographic analysis of the obtained α-olefin oligomers are shown along with other data in Tables 15–17.

In Tables 15–17, "h-1" indicating the additional component is tris(pentafluorophenyl)borane. "Contact method $A_1$" is a method in which α-olefin, chromium compound and additional component {tris(pentafluorophenyl)borane: $B(C_6F_5)_3$} are introduced into a solution containing pyrrole and alkylaluminum compound; "contact method $A_2$" is a method in which α-olefin and chromium compound are introduced into a solution containing pyrrole, alkylaluminum compound and additional substance; "contact method $D_1$" is a method in which α-olefin, chromium compound and pyrrole are introduced into a solution containing alkylaluminum compound and additional substance; and "contact method F" is a method in which α-olefin is introduced into a solution prepared by successively feeding the additional component, alkylaluminum compound, pyrrole and chromium compound.

TABLE 14

| | Example | | | |
|---|---|---|---|---|
| | 48 | 49 | 50 | 51 |
| Kind of solvent (amount: ml) | HP(50) | HP(50) | HP(50) | HP(50) |
| Kind of Cr compound | Cr-1 | Cr-1 | Cr-1 | Cr-1 |
| Amount of Cr compound (mg/hour) | 10 | 10 | 10 | 10 |
| Molar amount of Cr compound (mmol/hour) (a) | 0.021 | 0.021 | 0.021 | 0.021 |
| Molar amount of pyrrole (mmol/hour) (b) | 0.060 | 0.060 | 0.060 | 0.060 |
| Molar amount of $Et_3Al$ (mmol/hour) (c) | 0.400 | 0.400 | 0.400 | 0.400 |
| Molar ratio of catalyst components (a:b:c) | 1:3:19 | 1:3:19 | 1:3:19 | 1:3:19 |
| Kind of additional component | h-1 | h-1 | h-1 | h-1 |
| Molar amount of additional substance (mmol) | 0.020 | 0.020 | 0.100 | 0.020 |
| Reaction temperature (°C.) | 100 | 100 | 100 | 100 |
| Ethylene pressure (kg/cm²) | 35 | 35 | 35 | 35 |
| Reaction time (Hr) | 0.25 | 0.25 | 0.25 | 0.25 |
| Contacting method | $A_1$ | $A_2$ | $A_2$ | F |
| <Product yield (g/hour)> | 14.4 | 14.4 | 38.0 | 13.7 |
| <Compositional distribution (wt %)> | | | | |
| $C_4$ | 1.7 | 1.9 | 0.2 | 1.4 |
| $C_6$ (total) | 79.5 | 74.5 | 83.2 | 80.3 |
| 1-hexane content in $C_6$ (wt %) | 94.6 | 94.6 | 94.4 | 94.9 |
| $C_8$ | 2.7 | 3.0 | 0.5 | 2.1 |
| $C_{10-20}$ | 13.9 | 17.9 | 15.2 | 14.0 |
| $C_{22-30}$ | 1.4 | 2.0 | 0.5 | 1.3 |
| Wax | 0.0 | 0.0 | 0.0 | 0.0 |
| Polyethylene (by-product) | 0.5 | 0.3 | 0.3 | 0.7 |
| <Catalytic efficiency> | 1439 | 1439 | 3799 | 1367 |
| <Catalytic activity> | 53313 | 53328 | 140699 | 50616 |

TABLE 16

| | Example | | | |
|---|---|---|---|---|
| | 52 | 53 | 54 | 55 |
| Kind of solvent (amount: ml) | HP(50) | HP(50) | HP(50) | HP(50) |
| Kind of Cr compound | Cr-1 | Cr-1 | Cr-1 | Cr-1 |
| Amount of Cr compound (mg/hour) | 10 | 10 | 10 | 10 |
| Molar amount of Cr compound (mmol/hour) (a) | 0.021 | 0.021 | 0.021 | 0.021 |
| Molar amount of pyrrole (mmol/hour) (b) | 0.060 | 0.060 | 0.060 | 0.060 |
| Molar amount of Et$_3$Al (mmol/hour) (c) | 0.400 | 0.400 | 0.400 | 0.400 |
| Molar ratio of catalyst components (a:b:c) | 1:3:19 | 1:3:19 | 1:3:19 | 1:3:19 |
| Kind of additional component | h-1 | h-1 | h-1 | h-1 |
| Molar amount of additional substance (mmol) | 0.020 | 0.100 | 0.100 | 0.060 |
| Reaction temperature (°C.) | 100 | 60 | 45 | 100 |
| Ethylene pressure (kg/cm$^2$) | 35 | 35 | 35 | 35 |
| Reaction time (Hr) | 0.25 | 0.25 | 0.25 | 0.25 |
| Contacting method | D$_1$ | D$_1$ | D$_1$ | D$_1$ |
| <Product yield (g/hour)> | 19.1 | 23.0 | 24.7 | 33.2 |
| <Compositional distribution (wt %)> | | | | |
| C$_4$ | 1.2 | 0.3 | 0.7 | 0.3 |
| C$_6$ (total) | 79.1 | 85.5 | 81.8 | 82.8 |
| 1-hexene content in C$_6$ (wt %) | 94.4 | 95.3 | 94.8 | 94.2 |
| C$_8$ | 1.9 | 0.7 | 0.9 | 0.6 |
| C$_{10-20}$ | 15.7 | 11.3 | 14.3 | 15.2 |
| C$_{22-30}$ | 1.1 | 0.3 | 0.4 | 0.5 |
| Wax | 0.0 | 0.1 | 0.2 | 0.1 |
| Polyethylene (by-product) | 0.7 | 1.8 | 1.8 | 0.5 |
| <Catalytic efficiency> | 1910 | 2302 | 2476 | 3318 |
| <Catalytic activity> | 70729 | 85272 | 91720 | 122885 |

TABLE 17

| | Example | | | |
|---|---|---|---|---|
| | 56 | 57 | 58 | 59 |
| Kind of solvent (amount: ml) | HP(50) | HP(50) | HP(50) | HP(50) |
| Kind of Cr compound | Cr-1 | Cr-1 | Cr-1 | Cr-1 |
| Amount of Cr compound (mg/hour) | 10 | 10 | 10 | 10 |
| Molar amount of Cr compound (mmol/hour) (a) | 0.021 | 0.021 | 0.021 | 0.021 |
| Molar amount of pyrrole (mmol/hour) (b) | 0.060 | 0.060 | 0.060 | 0.060 |
| Molar amount of Et$_3$Al (mmol/hour) (c) | 0.400 | 0.400 | 0.200 | 0.400 |
| Molar ratio of catalyst components (a:b:c) | 1:3:19 | 1:3:19 | 1:3:10 | 1:3:19 |
| Kind of additional component | h-1 | h-1 | h-1 | h-1 |
| Molar amount of additional substance (mmol) | 0.004 | 0.004 | 0.004 | 0.004 |
| Reaction temperature (°C.) | 100 | 100 | 100 | 100 |
| Ethylene pressure (kg/cm$^2$) | 35 | 70 | 35 | 35 (H$_2$: 3.5 KG) |
| Reaction time (Hr) | 0.25 | 0.25 | 0.25 | 0.25 |
| Contact method | D$_1$ | D$_1$ | D$_1$ | D$_1$ |
| <Product yield (g/hour)> | 6.7 | 15.9 | 3.9 | 14.9 |
| <Compositional distribution (wt %)> | | | | |
| C$_4$ | 2.4 | 3.5 | 3.6 | 1.9 |
| C$_6$ (total) | 78.7 | 78.2 | 79.4 | 78.8 |
| 1-hexene content in C$_6$ (wt %) | 94.5 | 95.0 | 94.3 | 92.0 |
| C$_8$ | 3.5 | 3.9 | 3.6 | 2.2 |
| C$_{10-20}$ | 14.2 | 13.9 | 12.2 | 16.7 |
| C$_{22-30}$ | 1.1 | 0.5 | 0.8 | 0.4 |
| Wax | 0.1 | 0.0 | 0.1 | 0.0 |
| Polyethylene (by-product) | 0.1 | 0.1 | 0.3 | 0.1 |
| <Catalytic efficiency> | 667 | 1588 | 386 | 1488 |
| <Catalytic activity> | 24711 | 58797 | 14303 | 55111 |

Example 60 n-Heptane (980 ml), a n-heptane solution of pyrrole (1.244 mmol) and a n-heptane solution of triethylaluminum (8.000 mmol) were charged to a 2.4 liter autoclave same as used in Example 1 while chromium (III) 2-ethylhexanoate (200 mg, 0.420 mmol) made into a solution with n-heptane was charged to the catalyst feed pipe. A n-heptane solution of an antistatic agent A specified below (1 mg/l) also charged to the autoclave.

Antistatic agent A:

"ASA-3" (produced by Shell Chemical Co., Ltd.)

The composition thereof comprises 20 wt % of chromium (III) alkylsalicylate having C$_{14-18}$ alkyl group, 10 wt % of calcium salt of di-2-ethylhexyl sulfosuccinate, 45 wt % of copolymer (high polymeric electrolyte) of 2-methyl-5-vinylpyridine and methacrylic acid C$_{17}$ alkyl ester.

First, the autoclave was heated to a temperature of 40° C. and then ethylene was introduced thereinto from the catalyst feed pipe at a temperature of 40° C. The rupture plate was ruptured under ethylene pressure, introducing the chromium compound into the barrel of the autoclave to start oligomerization of ethylene. Ethylene was introduced until the overall pressure reached 35 kg/cm$^2$(G). Thereafter the overall pressure was kept at 35 kg/cm$^2$(G), while maintaining the temperature at 40° C. One hour later, ethanol was injected into the reaction mixture to terminate the reaction.

Then the same operations as in Example 1 were repeated to obtain α-olefin oligomers. In this example, no deposition of the by-product polymers took place on the inner wall of the autoclave. The results of compositional analysis of the obtained α-olefin oligomers by gas chromatography are shown along with other data in Table 18.

Examples 61 and 62

The same procedure as in Example 60 was conducted except for a change of reaction temperature, solvent and antistatic agent as shown in Table 18. The results of gas chromatographic analysis of the obtained α-olefin oligomers are shown along with other data in Table 18. In both examples, no deposition of the by-product polymers was observed on the inner wall of the autoclave. In the table, antistatic agents "B" and "C" are as specified below:

Antistatic agent B:
"Stadis 450" (produced by E. I. Du Pont de Neymours & Co.)

The composition thereof comprises 14 wt % of polybutene sulfate, 3 wt % of aminoethanolepichlorohydrin polymer, 13 wt % of alkylbenzenesulfonic acid, 70 wt % of toluene and trace amounts of quaternary ammonium salt of aliphatic alkyl and isopropyl alcohol.

Antistatic agent C:
"Stadis 425" (produced by E. I. Du Pont de Neymours & Co.)

The composition thereof comprises 2–7 wt % of polyaminopolyol, 2–8 wt % of dodecylbenzenesulfonic acid, 60–70 wt % of kerosine, 10–20 wt % of toluene, less than 0.017 wt % of benzene and 2–7 wt % of a mixed aromatic solvent ($C_{9-17}$).

TABLE 18

|  | Example | | |
|---|---|---|---|
|  | 60 | 61 | 62 |
| Antistatic agent | A | B | C |
| Kind of solvent (amount: liter) | HP(1) | HP(1) | HP(1) |
| Reaction temperature (°C.) | 40 | 60 | 60 |
| Ethylene pressure (Kg/cm$^2$) | 35 | 35 | 35 |
| Reaction time (Hr) | 1.0 | 1.0 | 1.0 |
| <Product yield (g/hour)> | 88.2 | 102.7 | 123.8 |
| <Compositional distribution (wt %)> | | | |
| $C_4$ | 12.2 | 15.3 | 18.0 |
| $C_6$ (total) | 74.7 | 74.2 | 71.6 |
| 1-hexane content in $C_6$ (wt %) | 96.2 | 95.7 | 96.0 |
| $C_8$ | 2.1 | 3.1 | 3.2 |
| $C_{10-20}$ | 20.2 | 6.8 | 6.7 |
| $C_{22-30}$ | 0.1 | 0 | 0 |
| Wax | 0 | 0 | 0 |
| Polyethylene (by-product) | 0.7 | 0.6 | 0.4 |
| <Deposition efficiency> | None | None | None |
| <Catalytic efficiency> | 441 | 513 | 619 |
| <Catalytic activity> | 4239 | 4936 | 5952 |

Example 63

A 2.4-liter autoclave dried by a dryer at 150° C. was assembled in a hot state and then the atmosphere in the autoclave was replaced with nitrogen in vacuum. A catalyst feed pipe equipped with a rupture plate and a stirrer equipped with a one-stage simple paddle-type (flat vane-type) blade had been attached to the autoclave. n-Heptane (980 ml), a n-heptane solution of pyrrole (1.244 mmol) and a n-heptane solution of triethylaluminum (8.000 mmol) were charged to the autoclave while a n-heptane solution of chromium (III) 2-ethylhexanoate (200 mg, 0.420 mmol) was charged to the catalyst feed pipe. The total amount of n-heptane was 1 liter.

First, the autoclave was heated to a temperature of 40° C. and then ethylene was introduced thereinto from the catalyst feed pipe at a temperature of 40° C. The rupture plate was ruptured under ethylene pressure to introduce the chromium compound into the autoclave, thus starting oligomerization of ethylene. The stirrer was operated at 400 r.p.m. and ethylene was introduced until the overall pressure reached 35 kg/cm$^2$(G). Thereafter the overall pressure was kept at 35 kg/cm$^2$(G), while maintaining the temperature at 40° C. One hour later, ethanol was injected into the autoclave to terminate the reaction.

After releasing ethylene from the autoclave, the by-product polymers (mostly polyethylene) in the reaction mixture were separated by filtration to obtain α-olefin oligomers. In this example, the by-product polymers were granular (100–300 μm in grain size) and the filtering operation could be performed very smoothly. The results of gas chromatographic analysis of the obtained α-olefin oligomers are shown along with other data in Table 19.

Examples 64 and 65

The same procedure as in Example 63 was conducted except for a change of reaction temperature and stirring speed as shown in Table 20. The results of compositional analysis of the obtained α-olefin oligomers are shown along with shape of the by-product polymers and other data in Table 19.

TABLE 19

|  | Example | | |
|---|---|---|---|
|  | 63 | 64 | 65 |
| Kind of solvent (amount: liter) | HP(1) | HP(1) | HP(1) |
| Reaction temperature (°C.) | 40 | 60 | 60 |
| Ethylene pressure (Kg/cm$^2$) | 35 | 35 | 35 |
| Reaction time (hour) | 1.0 | 1.0 | 1.0 |
| Stirring speed (r.p.m.) | 400 | 600 | 800 |
| <Product yield (g/hour)> | 102.7 | 102.7 | 102.5 |
| <Compositional distribution (wt %)> | | | |
| $C_4$ | 15.3 | 15.8 | 15.5 |
| $C_6$ (total) | 74.2 | 73.9 | 74.5 |
| 1-hexane content in $C_6$ (wt %) | 95.7 | 95.5 | 95.8 |
| $C_8$ | 3.1 | 2.9 | 3.3 |
| $C_{10-20}$ | 6.8 | 6.9 | 6.2 |
| $C_{22-30}$ | 0 | 0 | 0 |
| Wax | 0 | 0 | 0 |
| Polyethylene (by-product) | 0.61 | 0.50 | 0.50 |
| <Shape of PE> | Granular | Granular | Granular |
| <Grain size of PE (μm)> | 100–300 | 50–300 | 50–300 |
| <Catalytic efficiency> | 513 | 520 | 508 |
| <Catalytic activity> | 4936 | 5003 | 4888 |

Example 66 n-Heptane (4.90 liters), a n-heptane solution of pyrrole (6.22 mmol) and a n-heptane solution of triethylaluminum (40.00 mmol) were charged to a 10 liter autoclave same as used in Example 1, while a n-heptane solution of chromium (III) 2-ethylhexanoate (1.00 g, 2.10 mmol) was charged to the catalyst feed pipe. The total amount of n-heptane was 5 liters.

First, the autoclave was heated to a temperature of 40° C. and then ethylene was introduced thereinto from the catalyst feed pipe. The rupture plate was ruptured under ethylene pressure, introducing the chromium compound into the autoclave to start oligomerization of ethylene. Ethylene was introduced until the overall pressure reached 35 kg/cm$^2$(G). Thereafter the overall pressure was kept at 35 kg/cm$^2$(G), while maintaining the temperature at 40° C. One hour later, ethanol was injected into the autoclave to terminate the reaction. The resulting reaction mixture contained granular by-product polymers.

After releasing ethylene from the autoclave and then the obtained reaction mixture was supplied into a vertical "Sharples Super Decanter" (manufactured by Tomoe Kogyo Co., Ltd.) to separate the by-product polymers. The separation was conducted at an external bowl speed of 4,000 r.p.m. and an internal screw speed of 3,500 r.p.m. The by-product polymers assumed a favorable fluid state like powder and could be efficiently separated from the reaction mixture. The results of gas chromatographic analysis of the obtained α-olefin oligomers are shown along with other data in Table 20.

Examples-67 and 68

The same procedure as in Example 66 was carried out except for a change of reaction temperature and solvent as shown in Table 20. The results of compositional analysis of the obtained α-olefin oligomers are shown along with other data in Table 20. In both examples, granular polymers were formed as by-product polymers and these by-product polymers could be separated efficiently as in Example 66.

TABLE 20

|  | Example | | |
| --- | --- | --- | --- |
|  | 66 | 67 | 68 |
| Kind of solvent (amount: liter) | HP(5) | HP(5) | HP(5) |
| Reaction temperature (°C.) | 40 | 60 | 60 |
| Ethylene pressure (Kg/cm$^2$) | 35 | 35 | 45 |
| Reaction time (Hr) | 1.0 | 1.0 | 1.0 |
| <Product yield (g/hour)> | 441 | 514 | 619 |
| <Compositional distribution (wt %)> | | | |
| $C_4$ | 12.2 | 15.3 | 18.0 |
| $C_6$ (total) | 74.7 | 74.2 | 71.6 |
| 1-hexane content in $C_6$ (wt %) | 96.2 | 95.7 | 96.0 |
| $C_8$ | 2.1 | 3.1 | 3.2 |
| $C_{10-20}$ | 20.0 | 6.8 | 6.7 |
| $C_{22-30}$ | 0.1 | 0 | 0 |
| Wax | 0 | 0 | 0 |
| Polyethylene (by-product) | 0.7 | 0.6 | 0.4 |
| <Shape of PE> | Granular | Granular | Granular |
| <Catalytic efficiency> | 441 | 513 | 619 |
| <Catalytic activity> | 4239 | 4936 | 5952 |

Example 69

Octane (n-form: 90% by weight; i-form: 10% by weight) (980 ml), an octane solution of pyrrole (1.244 mmol) and an octane solution of triethylaluminum (8.000 mmol) were charged to a 2.4 liter autoclave same as used in Example 1 while an octane solution of chromium (III) 2-ethylhexanoate (200 mg, 0.420 mmol) was charged to the catalyst feed pipe. The total amount of octane was 1 liter.

First, the autoclave was heated to a temperature of 60° C. and then ethylene was introduced thereinto from the catalyst feed pipe at a temperature of 60° C. The rupture plate was ruptured under ethylene pressure, introducing the chromium compound into the autoclave to start oligomerization of ethylene. Ethylene was introduced until the overall pressure reached 35 kg/cm$^2$(G). Thereafter the overall pressure was kept at 35 kg/cm$^2$(G), while maintaining the temperature at 60° C. One hour later, ethanol was injected into the autoclave to terminate the reaction. After releasing ethylene from the autoclave and the by-product polymers (mostly polyethylene) in the reaction mixture were separated by filtration to recover the reaction mixture. The results of gas chromatographic analysis of the α-olefin oligomers in the reaction mixture are shown along with other data in Table 21 (Example 69A).

Then the reaction mixture was distilled and separated into an octane fraction, a fraction with 4–6 carbon atoms and a fraction with carbon atoms of not less than 8. The latter fraction was subjected to a hydrogenation treatment. This hydrogenation treatment was carried out at a temperature of 90° C. under a pressure of 40 kg/cm$^2$(G) by using a Pt/γ-alumina catalyst. The results of gas chromatographic analysis of the hydrogenation product are shown along with other data in Table 21 (Example 69A).

Then said octane fraction and the hydrogenation product were recycled to the oligomerization reaction system as a solvent and the same reaction as described above was repeated. The solvent composition in this reaction was total octane/$C_{10-20}$=98.9/1.1 (by weight). The results of gas chromatographic analyses of the α-olefin oligomers in the reaction mixture and said hydrogenation product are shown along with other data in Table 21 (Example 69B).

In Table 21, "OCT" denotes octane.

TABLE 21

|  | Example | |
| --- | --- | --- |
|  | 69A | 69B |
| Kind of solvent (amount: l) | OCT(1) | OCT/$C_{10-20}$(98.9/1.1) (1) |
| Reaction temperature (°C.) | 60 | 60 |
| Ethylene pressure (Kg/cm$^2$) | 35 | 35 |
| Reaction time (Hr) | 1.0 | 1.0 |
| <Product yield (g/Hr)> | 107.9 | 105.1 |
| <Compositional distribution (wt %)> | | |
| $C_4$ | 13.7 | 12.0 |
| $C_6$ (total) | 75.7 | 75.5 |
| 1-hexane content in $C_6$ (wt %) | 95.9 | 95.5 |
| $C_8$ | 2.9 | 3.8 |
| $C_{10-20}$ | 7.3 | 8.3 |
| $C_{22-30}$ | 0 | 0 |
| Wax | 0 | 0 |
| <Compositional distribution of hydrogenated fraction> | | |
| $C_8$ | 28.0 | — |
| $C_{10-20}$ | 72.0 | — |
| Polyethylene (PE) (by-product) | 0.4 | 0.4 |
| <Catalytic efficiency> | 540 | 536 |
| <Catalytic activity> | 5189 | 5151 |

Example 70

In Example 60, after the by-product polymers (mostly polyethylene) in the reaction mixture have been separated from the reaction mixture, the filtrate was introduced into a 2-liter vessel equipped a condenser and stirrer, and extracted with a 10% HNO$_3$ aqueous solution (organic layer/aqueous layer=1/1(v/v)) at a temperature of 50° C. for one hour with stirring. Thereafter, stirring was stopped and the solution was left still. Concentration of the metallic substances in the separated aqueous layer was determined by high-frequency plasma emission spectroscopic analysis. As a result, chromium and alumina were detected, and their amount as determined from the calculation of concentration was substantially same as the amount used as catalyst components in the reaction.

Example 71

The same procedure as in Example 70 was conducted except that 20% NaOH aqueous solution was used instead of 10% HNO₃ aqueous solution. Chrominum and aluminum were recovered in NaOH aqueous solution, quantitatively.

Example 72

1-Hexene (980 ml), a n-heptane solution of pyrrole (1.244 mmol) and a n-heptane solution of triethylaluminum (8.000 mmol) were charged to a 2.4 liter autoclave same as used in Example 1 while a heptane solution of chromium (III) 2-ethylhexanoate (200 mg, 0.420 mmol) was charged to the catalyst feed pipe. The total amount of 1-hexene and n-heptane was 1 liter.

First, the autoclave was heated to a temperature of 60° C. and then ethylene was introduced thereinto from the catalyst feed pipe at a temperature of 60° C. The rupture plate was ruptured under ethylene pressure to introduce the chromium compound into the autoclave to start oligomerization of ethylene. Ethylene was introduced until the overall pressure reached 35 kg/cm²(G). Thereafter the overall pressure was kept at 35 kg/cm²(G), while maintaining the temperature at 60° C. One hour later, ethanol was injected into the autoclave to terminate the reaction.

After releasing ethylene from the autoclave, the by-product polymers (mostly polyethylene) in the reaction mixture were separated by filtration to obtain α-olefin oligomers. The results of gas chromatographic analysis of the obtained α-olefin oligomers are shown along with other data in Table 22.

In Table 22, "HEX" denotes 1-hexene and "OCTE" denotes 1-octene. Amount is the combined amount of α-olefin and solvent.

Example 73

The same procedure as in Example 72 was conducted except that 1-octene (980 ml) was used in place of 1-hexene (980 ml). The results are shown in Table 22.

TABLE 22

|  | Example 72 | Example 73 |
|---|---|---|
| Kind of α-olefin (amount: l) | HEX(1) | OCTE(1) |
| Reaction temperature (°C.) | 60 | 60 |
| Ethylene pressure (Kg/cm²) | 35 | 35 |
| Reaction time (Hr) | 1.0 | 1.0 |
| <Product yield (g/hour)> | 75.2 | 111.4 |
| <Compositional distribution (wt %)> | | |
| $C_{10}$ | 29.2 | 4.3 |
| $C_{12}$ | 0.8 | 22.7 |
| $C_4$ | 18.4 | 13.7 |
| $C_6$ | 43.2 | 46.9 |
| $C_8$ | 5.3 | 9.2 |
| $C_{14-20}$ | 2.7 | 2.6 |
| $C_{22-30}$ | 0 | 0.1 |
| Wax | 0 | 0 |
| Polyethylene (PE) (by-product) | 0.4 | 0.6 |
| <Catalytic efficiency> | 376 | 557 |
| <Catalytic activity> | 3613 | 5355 |

What is claimed is:

1. A process for preparing α-olefin oligomers, which comprises oligomerizing an α-olefin in a hydrocarbon solvent by reacting said α-olefin at a temperature of 0° to 250° C. under atmospheric pressure to 250 kg/cm² in a chromium-based catalyst system composed of a combination of at least a chromium compound, an amine or metal amide, and alkylaluminum compound, provided that before the α-olefin, the chromium compound, the amine or metal amide and the alkylaluminum compound come into contact with each other, the chromium compound and the alkylaluminum compound do not previously contact each other, and further provided that when any of the chromium compound, the amine or metal amide and the alkylaluminum compound is made into a solution, the solution is prepared using a hydrocarbon solvent.

2. The process according to claim 1, wherein the chromium compound is selected from the group consisting of chromium alkoxides, chromium carboxylates, chromium β-diketonates, chromium salts of anion of β-ketoesters, chromium β-ketocarboxylates, amide complexes of chromium, carbonyl complexes of chromium, carbone complexes of chromium, cyclopentadienyl complexes of chromium, alkyl complexes of chromium, phenyl complexes of chromium, chromium halides, ether complexes of chromium halide, ester complexes of chromium halide, ketone complexes of chromium halide, aldehyde complexes of chromium halide, alcohol complexes of chromium halide, amine complexes of chromium halide, nitrile complexes of chromium halide, phosphine complexes of chromium halide and thioether complexes of chromium halide.

3. The process according to claim 1, wherein the amine or metal amide is a primary or secondary amine, or the corresponding metal amide derived therefrom.

4. The process according to claim 1, wherein the alkylaluminum compound is one represented by the following formula (1):

$$R^1{}_mAl(OR^2)_nH_pX_q \qquad (1)$$

wherein $R^1$ and $R^2$ are each a hydrocarbon group having 1 to 15 carbon atoms and may be the same or different from each other; X is a halogen atom; m, n, p and q are the numbers defined by the following relations: $0<m\leq 3$, $0\leq n<3$, $0\leq p<3$, $0\leq q<3$, and $m+n+p+q=3$.

5. The process according to claim 4, wherein the alkylaluminum compound represented by the formula (1) is a trialkylaluminum represented by the formula (2), a halogenated alkylaluminum compound represented by the formula (3), an alkoxyalkylaluminum compound represented by the formula (4) or an alkylaluminum hydride compound represented by the formula (5):

$$R^1{}_3Al \qquad (2)$$

$$R^1{}_mAlX_{3-m}(1.5\leq m<3) \qquad (3)$$

$$R^1{}_mAl(OR^2)_{3-m}(0<m<3) \qquad (4)$$

$$R^1{}_mAlH_{3-m}(0<m<3) \qquad (5)$$

as in claim 4.

6. The process according to claim 1, wherein an α-olefin and a chromium compound are introduced into a solution containing an amine or metal amide, and an alkylaluminum compound.

7. The process according to claim 1, wherein an α-olefin and an alkylaluminum are introduced into a solution containing a chromium compound and an amine or metal amide.

8. The process according to claim 1, wherein an α-olefin, an amine or metal amide, and an alkylaluminum compound are introduced into a solution containing a chromium compound.

9. The process according to claim 1, wherein an α-olefin, a chromium compound and an amine or metal amide are introduced into a solution containing an alkylaluminum compound.

10. The process according to claim 1, wherein a chromium compound, an amine or metal amide, an alkylaluminum compound and an α-olefin are introduced into a reactor simultaneously and separately.

11. The process according to claim 1, wherein the molar ratio of (a) a chromium compound, (b) an amine or metal amide, and (c) an alkylaluminum compound is=1:2 to 4:4 to 8.

12. The process according to claim 11, wherein the reaction is carried out at a temperature of 0° to 70° C.

13. The process according to claim 1, wherein the reaction is carried out in the presence of a non-coordinating Lewis acid-containing compound.

14. The process according to claim 1, wherein the reaction is carried out in the presence of a non-conjugated diene compound.

15. The process according to claim 1, wherein the reaction is carried out in the presence of an aromatic hydrocarbon compound.

16. The process according to claim 1, wherein the solvent is an acyclic or alicyclic saturated hydrocarbon having 4 to 7 carbon atoms.

17. A process for preparing α-olefin oligomers, which comprises oligomerizing an α-olefin in a solvent by reacting said α-olefin at a temperature of 0° to 250° under atmospheric pressure or a pressure up to 250 kg/cm$^2$ in a chromium-based catalyst system composed of a combination of at least a chromium compound, an amine or metal amide, an alkylaluminum compound and a non-coordinating Lewis acid-containing compound represented by the formula (6):

wherein M$^1$ is an element selected from the group consisting of IIIB, IVB, VB and VIB Groups in the periodic table; R$^1$ to R$^4$ are each an organic group, inorganic group or an anionic atom; and $^+$is a cation containing an element selected from the group consisting of IA, VIIA, VIII, IB and IIIB, IVB, VB and VIB Groups in the periodic table.

18. The process according to claim 17, wherein R$^1$ to R$^4$ in the compound represented by the formula (6) are respectively a dialkylamino group, alkoxy group having 1–20 carbon atoms, aryloxy group having 6–20 carbon atoms, alkyl group having 1–20 carbon atoms, aryl group having 6–20 carbon atoms, alkylaryl group having 7–20 carbon atoms, arylalkyl group having 7–20 carbon atoms, halogen substituted hydrocarbon group having 1–20 carbon atoms, acyloxy group having 1–20 carbon atoms, alkoxyaryl group having 7–20 carbon atoms, halogen-substituted alkoxyaryl group having 7–20 carbon atoms, organic metalloid group or halogen atom, and two or more of R$^1$ to R$^4$ may be combined to form a ring.

19. The process according to claim 17, wherein L in the compound of the formula (6) is represented by the formula: M$^3$, M$^4$R$^8$R$^9$, E$^1$R$^{10}$R$^{11}$R$^{12}$ or E$^2$R$^{13}$R$^{14}$R$^{15}$R$^{16}$, wherein M$^3$ is an element selected from the group consisting of IA, IB and IIIB Groups in the periodic table; M$^4$ is an element selected from the group consisting of VIIA and VIII Groups; E$^1$ is a carbon atom, oxygen atom or sulfur atom; E$^2$ is a nitrogen atom or phosphorus atom; R$^8$ and R$^9$ are each cyclopentadienyl group, substituted cyclopentadienyl group, indenyl group or fluorenyl group, and they may be combined to form a ring; R$^{10}$ to R$^{16}$ are each a hydrogen atom, halogen atom, alkyl group having 1–20 carbon atoms, aryl group having 6–20 carbon atoms, alkylaryl group having 7–20 carbon atoms, arylalkyl group having 7–20 carbon atoms or organic metalloid group.

20. The process according to claim 17, wherein an α-olefin and a chromium compound are introduced into a solution containing an amine or metal amide, an alkylaluminum compound and a non-coordinating Lewis acid-containing compound.

21. The process according to claim 17, wherein an α-olefin, a chromium compound and an amine or metal amide are introduced into a solution containing an alkylaluminum compound and a non-coordinating Lewis acid-containing compound.

22. The process according to claim 17, wherein an α-olefin and an alkylaluminum compound are introduced into a solution containing a chromium compound, an amine or metal amide and a non-coordinating Lewis acid-containing compound.

23. The process according to claim 17, wherein the oligomerization reaction of an α-olefin is carried out in a saturated hydrocarbon solvent having not more than 7 carbon atoms at a temperature of 0° to 70° C., and then the by-product polymers in the reaction mixture are separated and removed to recovery the α-olefin oligomers without melting the by-product polymers.

24. The process according to claim 17, wherein the reaction mixture is supplied into a solid/liquid separating apparatus in which the solid matter is separated by centrifugation and the separated solid matter is discharged out of the system by a rotary screw, whereby the granular by-product polymers in said reaction mixture are separated.

25. The process according to claim 17, wherein the oligomerization reaction of an α-olefin is carried out in a saturated hydrocarbon solvent, then the by-products are separated away from the reaction mixture, a part of the resultant α-olefin oligomers is converted into the corresponding saturated hydrocarbons by hydrogenation, and said saturated hydrocarbons are recycled to the oligomerization reaction system.

26. The process according to claim 17, wherein the reaction mixture containing the catalyst components is contacted with an acidic or alkaline aqueous solution after oligomerization to remove the catalyst components.

27. The process according to claim 17, wherein α-olefin is ethylene and the main product of the α-olefin oligomerization is 1-hexene.

28. The process according to claim 27 which comprises carrying out oligomerization of ethylene in a reaction solvent having a higher boiling point than that of 1-hexene under a pressure of not less than 10 kg/cm$^2$(G) to obtain an α-olefin oligomer composition containing 1-hexene, then reducing the pressure of the reaction system to not more than 3 kg/cm$^2$(G) by degassing, and separating the by-products therefrom.

29. The process for producing 1-hexene according to claim 28, wherein the oligomerization reaction of ethylene is carried out to obtain an α-olefin oligomer composition with a 1-hexene content of not less than 50 wt %, then 1-hexene and a reaction solvent are distilled out from a reaction mixture containing said reaction solvent and α-olefin oligomer composition, and the recovered reaction solvent is recycled to the reaction system.

30. The process for producing 1-hexene according to claim 28, wherein said oligomerization reaction is carried out in the presence of hydrogen.

31. A process for preparing α-olefin oligomers, which comprises oligomerizing an α-olefin in a solvent by reacting said α-olefin at a temperature of 0° to 250 °C. under atmospheric pressure or a pressure of 250 kg/cm² in a chromium-based catalyst system composed of a combination of at least a chromium compound, an amine or metal amide, an alkylaluminum compound and a non-coordinating Lewis acid-containing compound represented by the formula (7):

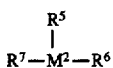

wherein $M^2$ is B and $R^5$ to $R^7$ are each an organic group or an inorganic group.

32. The process according to claim 31, wherein $R^5$ to $R^7$ in the compound of formula (7) are independently selected from the group consisting of a dialkylamino group, alkoxy group having 1–20 carbon atoms, aryloxy group having 6–20 carbon atoms, alkyl group having 1–20 carbon atoms, aryl group having 6–20 carbon atoms, alkylaryl group having 7–20 carbon atoms, arylalkyl group having 7–20 carbon atoms, halogen-substituted hydrocarbon group having 1–20 carbon atoms, acyloxy group having 1–20 carbon atoms, alkoxyaryl group having 7–20 carbon atoms, halogen-substituted alkoxyaryl group having 7–20 carbon atoms, organic metalloid group or halogen atom, provided that two or more of $R^5$ to $R^7$ may be combined to form a ring.

33. The process according to claim 31, wherein the α-olefin and chromium compound are introduced into a solution containing an amine or metal amide, an alkylaluminum compound and a non-coordinating Lewis acid-containing compound.

34. The process according to claim 31, wherein the α-olefin, chromium compound and amine or metal amide are introduced into a solution containing an alkylaluminum compound and a non-coordinating Lewis acid-containing compound.

35. The process according to claim 31, wherein the α-olefin and alkylaluminum compound are introduced into a solution containing a chromium compound, an amine or metal amide and a non-coordinating Lewis acid-containing compound.

36. The process according to claim 1, wherein the α-olefin is ethylene and the oligomerization is carried out under ethylene pressure.

37. The process according to claim 31, wherein the amount of the chromium compound is $1.0 \times 10^{-7}$ to 0.5 mol based on one liter of the solvent.

38. The process according to claim 31, wherein the amount of the alkylaluminum compound is 50 mmol to $1.0 \times 10^4$ mol based on one mol of the chromium compound.

39. The process according to claim 31, wherein the amount of the amine or metal amide is not less than 0.001 mol based on one mol of the chromium compound.

40. The process according to claim 31, wherein the amount of the non-coordinating Lewis acid-containing compound is not less than 0.001 mol based on one mol of the chromium compound.

41. A process for preparing α-olefin oligomers, which comprises oligomerizing an α-olefin in a hydrocarbon solvent by reacting said α-olefin at a temperature of 0° to 250° C. under atmospheric pressure to 250 kg/cm² in a chromium-based catalyst system composed of a combination of at least a chromium compound, an amine or metal amide, and an alkylaluminum compound, provided before the oligomerization of the α-olefin takes place, the chromium compound and the alkylaluminum compound do not previously contact each other, and further provided that when any of the chromium compound, the amine or metal amide and the alkylaluminum compound is made into a solution, the solution is prepared using a hydrocarbon solvent.

42. A process for preparing α-olefin oligomers, which comprises oligomerizing an α-olefin in a hydrocarbon solvent by reacting the α-olefin at a temperature of 0° to 250° C. under atmospheric pressure to 250 kg/cm² in a chromium-based catalyst system composed of a combination of at least a chromium compound, an amine or metal amide, and an alkylaluminum compound, wherein the chromium compound and the alkylaluminum compound contact each other for the first time when the α-olefin comes into contact with all of the components of the catalyst system, provided that before the α-olefin, the chromium compound, the amine or metal amide and the alkylaluminum compound come into contact with each other, the chromium compound and the alkylaluminum compound do not previously contact each other, and further provided that when any of the chromium compound, the amine or metal amide and the alkylaluminum compound is made into a solution, the solution is prepared using a hydrocarbon solvent.

* * * * *